(12) United States Patent
Hu et al.

(10) Patent No.: US 6,225,321 B1
(45) Date of Patent: May 1, 2001

(54) LONG ANALGESIC ACTING NALBUPHINE POLYESTER DERIVATIVE AND METHOD OF USE

(76) Inventors: Oliver Yoa-Pu Hu, No. 18 Sh-Yuan Street; Shung-Tai Ho, 1F, No. 36, Sec. 3, Ting-Chow Rd., both of Taipei; Fangchen Lee, No. 59 Yu Shih Road, Youth Industrial District, Tachia, all of (TW)

( * ) Notice: Subject to any disclaimer, the term of this patent is extended or adjusted under 35 U.S.C. 154(b) by 0 days.

(21) Appl. No.: 08/869,917

(22) Filed: Jun. 5, 1997

(51) Int. Cl.$^7$ ............ C07D 489/02; A61K 31/485
(52) U.S. Cl. ............... 514/282; 546/43; 546/44; 546/45; 546/46
(58) Field of Search ............... 546/43, 44, 45, 546/46; 514/282

(56) References Cited

U.S. PATENT DOCUMENTS

| | | | |
|---|---|---|---|
| 4,464,378 | * | 8/1984 | Hussain ............... 424/260 |
| 4,668,685 | * | 5/1987 | Shami ............... 514/279 |
| 4,673,679 | * | 6/1987 | Aungst et al. ............ 514/282 |
| 4,722,928 | * | 2/1988 | Boswell et al. ............ 514/282 |

FOREIGN PATENT DOCUMENTS

615756 * 9/1994 (EP) .

OTHER PUBLICATIONS

Hu et al., Chem. Abstract 124:212061, 1996.*

* cited by examiner

*Primary Examiner*—Richard L. Raymond
*Assistant Examiner*—Deepak Rao

(57) ABSTRACT

The nalbuphine polyester derivative is related to a novel long acting agent. The nalbuphine polyester derivative is R—[CO-NAL]$_n$ wherein n is an integer from 2–4 and, in which the R is selected from a saturated or nonsaturated, substituted or unsubstituted, aliphatic or aromatic group having 1 to 40 carbon atoms. The process for producing the derivative includes esterifying nalbuphine with a saturated or unsaturated fatty acid or a halogen compound of the fatty acid with an acid anhydride. A pharmaceutical composition contains the derivative and a pharmaceutically acceptable carrier, which can be administered to an animal or person for treating pain.

17 Claims, 14 Drawing Sheets

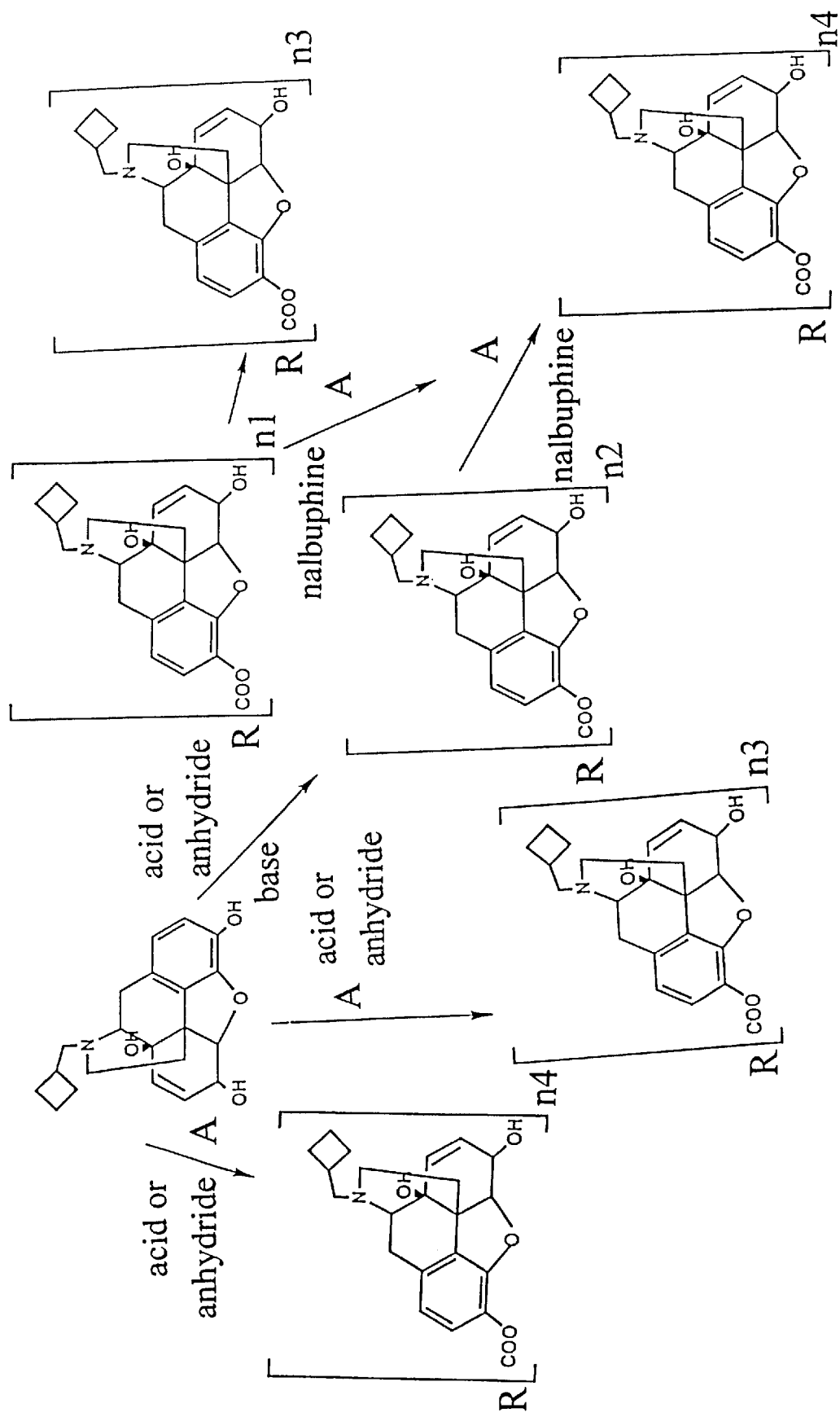
FIG 1-A

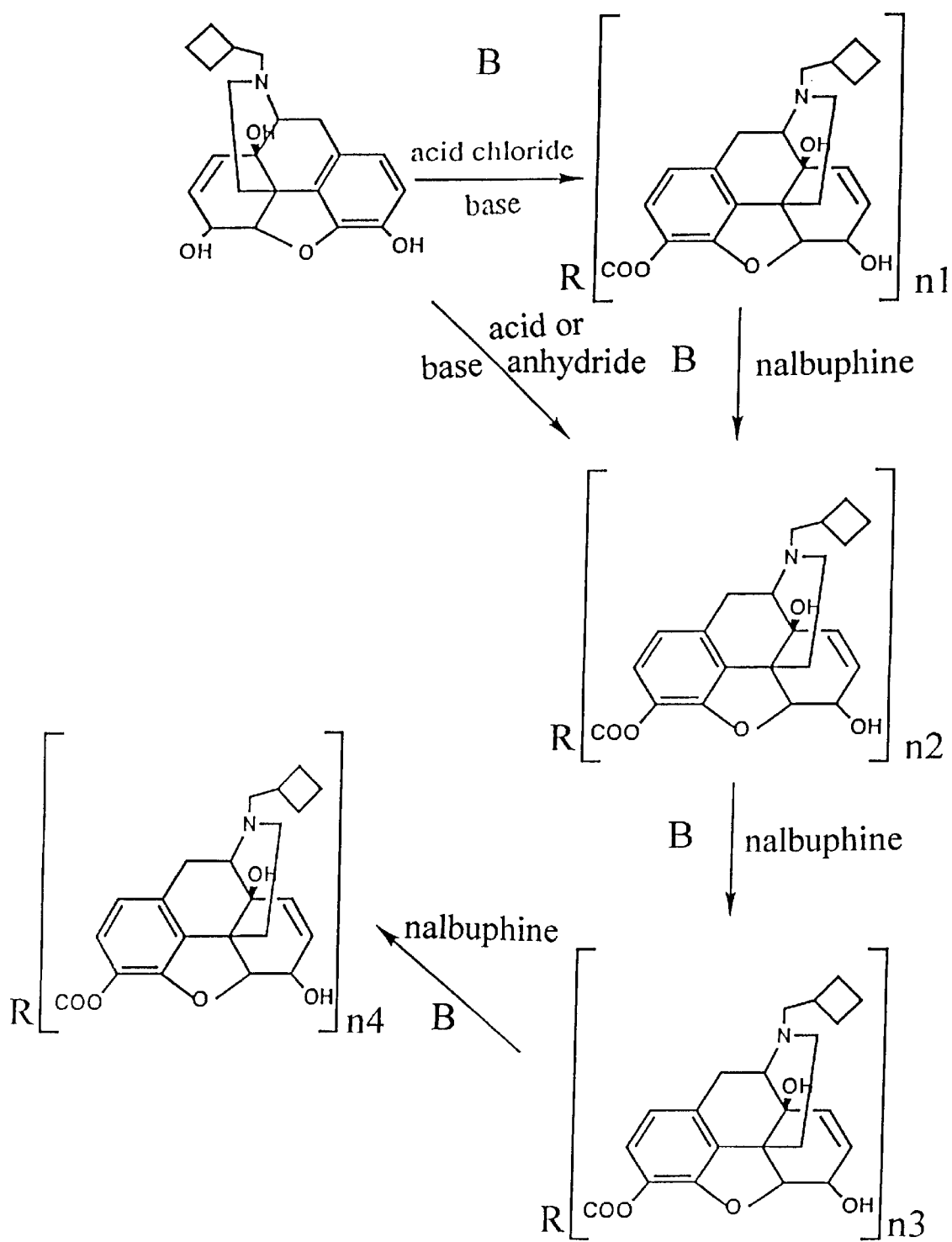
n1-n4=1,2,3,4, n4 > n3 > n2 > n1
FIG 1-B

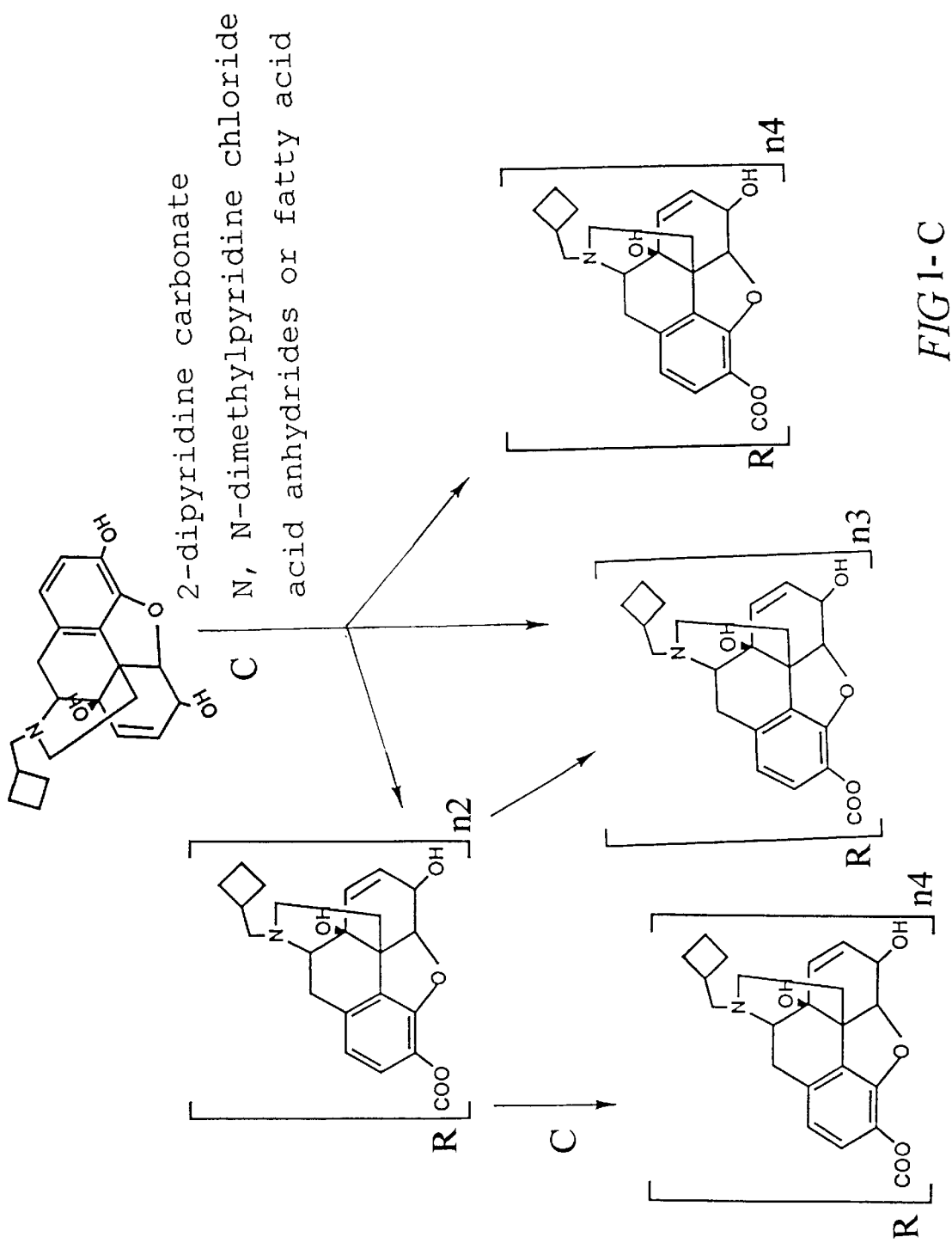
FIG 1-C

50% PA

LONG ANALGESIC ACTING NALBUPHINE POLYESTER DERIVATIVE AND METHOD OF USE

BACKGROUND OF THE INVENTION

1. Field of the Invention

This invention relates to long acting analgesics Nalbuphine polyester derivative and to pharmaceutical compositions comprising those compounds.

2. Description of the Related Art

New type of opiods drugs such as Buprenorphine, Nalbuphine, Butorphanol, so-called narcotic agonist-antagonist analgesics have been developed. They exhibit a dual action of agonist and antagonist on opiods-receptors as reported by Schmidt, W. K. et al (*Drug Alcohol Depend.* 14, 339, 1985), where pointed out that dual action of those drugs not only had high affinity to opium receptor but also served as anatagonist. For example, Nalbuphine was the antagonist for Mu receptor and agonist for Kappa receptor. Those agonist/antagonist drugs have improvement on untoward effects of opiods drugs, such as addiction and respiratory suppression.

Shafer, S. L. et al. have investigated the analgesic potency of narcotic agonist-antagonist analgesics. They have found that when compared with the more opiods drugs to elicit the same analgesic effect, the dose needed for Morphine and Nalbuphine are 10 mg; for Buprenorphine is 0.3 mg; for Butorphanol is 2 mg (*Anesthesiology*, 74, 53, 1991). According to the publication by Schmidt, W. K. et al, supra (1985), Nalbuphine is the most widely used one and has excellent therapeutic efficacy. After continuous use of Nalbuphine for 6 months, no significant addiction and addition was found. Those narcotic agonist-antagonist analgesics exhibits only slight respiratory inhibition. In clinical use, Nalbuphine is safer than the traditional narcotic analgesics.

An ideal analgesic should exhibit short onset time, should be long acting, potent, should cause no addiction, no inhibition of the cardiac or cardiovascular system, no respiratory inhibition, and should have few other adverse effects which were suggested by Bovill, J. G. et al. (*Drugs*, 33, 520, 1987). For the relief of pain, local anesthetics like Xylocaine or Bupivacaine can only be applied to restricted areas. In addition, local anesthetics are short acting and even when they are given intracerebroventricularly, the duration of action hardly exceeds 6 hours. Therefore, for the severe and acute pain caused by cardiac, pulmonary, abdominal, osteopathia, and obstetrical surgery, severe burn injury and terminal stage of cancer, local anesthetics are not satisfactory.

Non-narcotic analgesics, such as Acetaminophen and aspirin can relieve pain of only low intensity, such as pain due to headache or toothache but they do not help in the case of serious pain. Bovill, J. G. et al. reported in *Drugs* volume 33, page 520 regarding that a strong narcotic analgesic drug should have action on Mu receptor in central nervous system. Hayes, A. G. et al. (*Br. J. Pharmacol.* Vol 79, 731, 1983) have reported that all the narcotic analgesics exhibit the same disadvantages with respect to addiction, and addition and respiratory inhibition. In addition, the duration of action of the narcotic analgesics is somewhat short. Normally, to maintain the analgesic effect, the dosing interval needs to be set at 3–5 hours. Even when the agent is administered to the spinal marrow, the duration of action could not be longer than 48 hours.

According to Schmidt, W. K. et al. suggested and clinical cases found that Nalbuphine was widely used in those narcotic agonist-antagonist analgesics. Nalbuphine has been found to be effective in controlling severe and deep pain caused by cardiac, pulmonary, abdominal, osteopathia, and obstetrical surgery, severe burn injury and the terminal stages of cancer via various parenteral administration routes, such as intramuscular, intravenous, intrathecal and intracerebroventricularly. However, the duration of analgesic action was short. According to Wang, J. J. et al. revealed data in 1985 *Ma Tsui Hsueh Tsa Chi*, volume 23, page 3, regarding the duration for different administration routes for Nalbuphine. For intravenous parenteral administration, the analgesic effect was maintained 3 to 5 hours, for intracerebro-ventricularly it was maintained 6 to 8 hours. For dramatic pain that needed hospitalization, multiple regiments were needed, and the medication cost was highly increased.

A Nalbuphine analogue compound was found in U.S. Pat. No. 4,673,679 which discloses the 3-morphine derivatives, in which the substitution group R was methyl, propyl, methyl propyl, methyl cyclopropyl, cyclopentyl; $R_1$ and $R_2$ were hydrogen and carboxyl groups respectively, $R_2$ could also be lactone or methylene groups; $R_3$ and $R_4$ were hydrogens or bonded to oxygen; $R_5$ was an alkanoyl group containing 2 to 18 carbons, or benzoyl, halides. They also disclose pharmaceutical dosage forms for sublingual, buccal, or nasal administration.

WO patent No. 82/03,768 revealed that narcotic antagonists, narcotic analgesics and related compounds such as Nalbuphine were prepared with a pH adjusting agent, jelling agent, emulsifier, emollient, cellulose derivatives, Tween 80, etc. and dosage forms such as nasal solution, nasal suspension, nasal ointment, and nasal jelly, containing those compounds which are adapted for nasal administration. European patent A1 No. 0,170,090 revealed the substituted benzolate ester prodrug derivative of 3-hydroxy-morphinans. Those compounds are useful as analgesics or narcotic antagonists, and provide dosage forms for capsules, tablets, suspensions, suppositories, and injections. U.S. Pat. No. 4,722,928 revealed N-oxide prodrug derivative of 3-hydroxy-morphine and partial morphinan analgesics, agonist-antagonists, and narcotic antagonists are useful therapeutic effects. Those compounds where prepared in various dosage forms with diluents, carriers such as magnesium stearate, cellulose derivatives, lactose, starch for tablets, powder, capsules, suspensions, syrups etc. for orally administration dosage forms. In view of the forgoing, it is apparent that all of these patents which contained Nalbuphine but didn't include Nalbuphine polyester derivative.

SUMMARY OF THE INVENTION

In one aspect, the present invention discloses a four-part invention; a new compound, a novel pharmaceutical acceptable long acting parenteral dosage forms or various pharmaceutical dosage forms for orally, oily parenteral administration and other administration, a process for synthesis the Nalbuphine polyester derivative, and a process for preparing the Nalbuphine polyester derivative clear parenteral dosage forms.

The present invention provides a new compound. The chemical structure of Nalbuphine polyester derivative is shown in Formula IV, in which R is selected from a nonsaturated aliphatic fatty acid, or saturated aliphatic fatty acid; n represents the number of ester groups in Nalbuphine polyester derivative and is an integer in the range of 1 to 4. When R is described by R'CO, the R' denotes the aliphatic group consisting of alkyl or alkylene having 1 to 40 carbon atoms. The aliphatic group is selected from a straight alkyl group, a branched alkyl group, a straight alkyl group substituted with a benzene ring, a branched alkyl group substituted with a benzene ring, a benzenyl group where the benzene ring contains a straight chain aliphatic group, or a benzenyl group where the benzene ring contains a branched chain of an aliphatic group. The synthesis methods of Nalbuphine polyester derivative have three types.

The present invention provides a pharmaceutically acceptable long acting parenteral dosage forms, which is administered once a day, or once for several days. Even when large amounts are administered, the occurrence of untoward effects were minimized. The advantage of the present invention are described as above, such as long duration, untoward effects, and safety that should improve therapeutic quality. The dosing interval can be set longer than 24 hours instead of 3–5 hours for post-operation patient. For last cancer stage patient's administration of the present invention dosage forms, instead of hospitalization can be given the same therapeutic efficacy.

In another aspect, the present invention was designed as a soft drugs which would release bioactive Nalbuphine in the animal body. In general, drug are metabolized into active forms and inactive forms. The soft drug Nalbuphine polyester derivative would only release bioactive Nalbuphine in the animal body. The new salts types, new stereoisomers types, and prodrugs are organized new drugs by US FDA and other countries. Usually only one of 7,000 new drugs where in the R & D process makes a marketable drug, since those R & D new drugs are selected by pharmaconogical tests and toxicological tests. The soft drug Nalbuphine polyester derivative which releases bioactive Nalbuphine, will make a marketable drug shortly.

In yet another aspect, the present invention provides various pharmaceutical dosage forms for oral, oily parenteral administration and other administration. The soft drug Nalbuphine polyester derivative is safe. In an emergency, such as acute pain, a single dosage has excellent therapeutic effects to maintain the analgesic effect duration 4–5 days in the animal body.

Last, the present invention provides a process for preparing the Nalbuphine polyester derivative clear parenteral dosage forms, which have more stabilization than various Nalbuphine dosage forms.

The invention will now be described by way of example with reference to the accompanying in which: Tables and Figures Table 1 depicts the physical properties of products.

Table 2 depicts the half-lives in various animal blood of the soft drug.

Table 3 depicts the half-lives in various animal blood of soft drug.

Table 4 depicts the excipients in a pharmaceutical composition.

Table 5 depicts the stability test for pharmaceutical compositions.

Table 6 depicts pharmacokinetic parameters of dinalbuphine obtained upon injection of Sebacoyl dinalbuphine (SDN) long acting preparation 30 mg/kg to five Beagle dogs.

Table 7 depicts pharmacokinetic parameters of dinalbuphine obtained upon injection of dose of Sebacoyl dinalbuphine (SDN) long acting preparation in the same Beagle dogs.

Table 8 depicts products and materials as examples.

BRIEF DESCRIPTION OF THE DRAWINGS

FIG. 1A–1C depicts the synthesis of Sebacoyl dinalbuphine.

DETAILED DESCRIPTION

Figure 2:
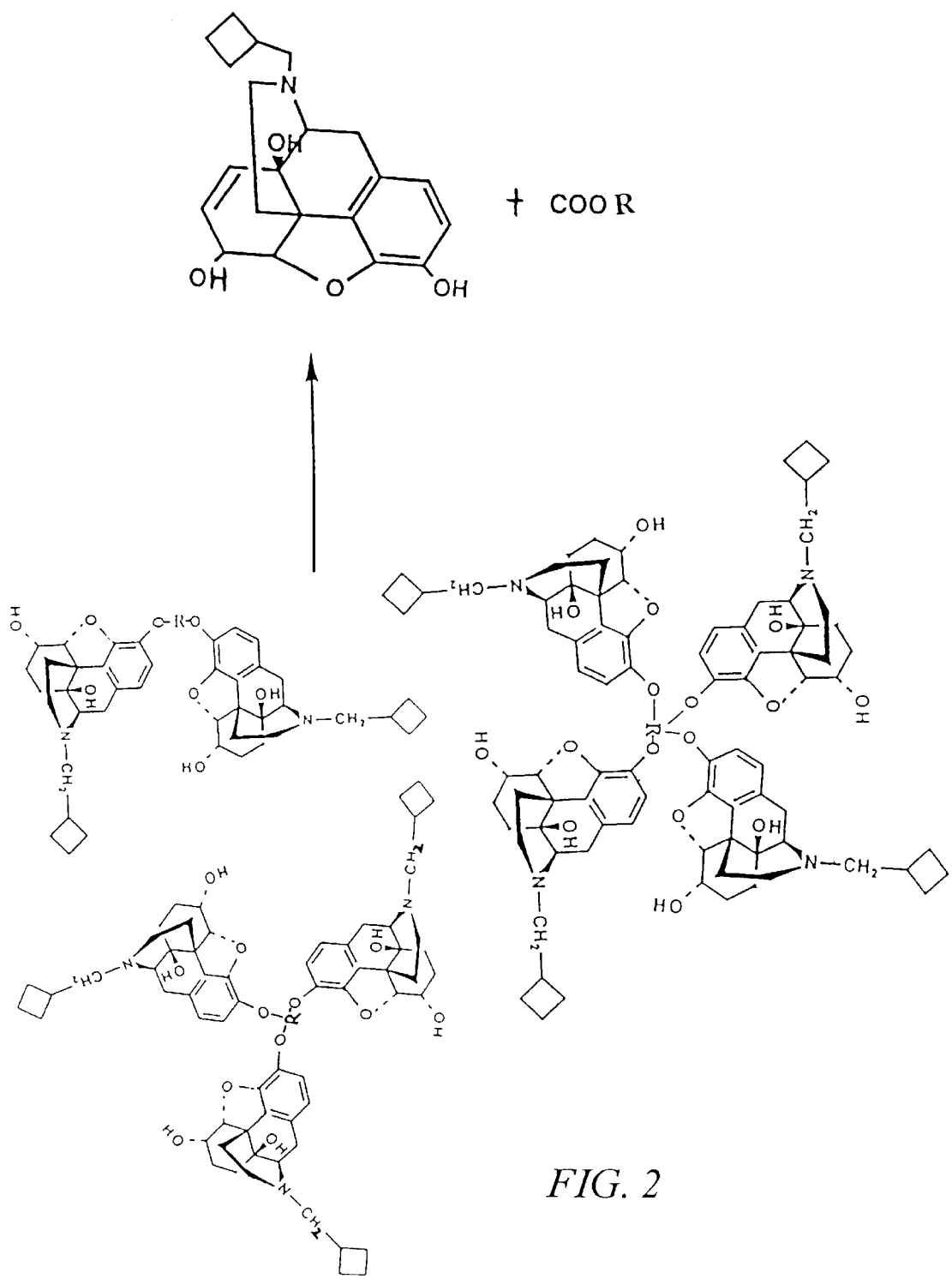
FIG. 2 depicts the metabolism of soft drug sebacoyl dinalbuphine(II, III).

The present invention, Nalbuphine polyester derivative is related to a novel long acting agent. The chemical structure of Nalbuphine polyester derivative is shown in Formula IV. The present invention also provides the process of preparation and the long acting preparations of pharmaceutical composition comprising i the Nalbuphine polyester derivative. The Nalbuphine polyester derivative can be formulated into various dosage forms. The present invention also provides the preparation method to produce a clear injection solution, in contrast to traditional suspensions.

The analgesic effect produced by a single dose of Nalbuphine polyester derivative lasts for 4 to 5 days, and such effect is adequate enough for the treatment of acute and chronic pain.

Chemical Structure Of Nalbuphine Polyester Derivative And Synthesis Method

The present invention, Nalbuphine polyester derivative is related to a novel long acting agent. The chemical structure of Nalbuphine polyester derivative is shown in Formula IV-a or IV-b, in which n represents the number of ester groups in the Nalbuphine polyester derivative, is an integer in the range of 1 to 4. The R is selected from a nonsaturated aliphatic fatty acid, or saturated aliphatic fatty acid. The Structure II, III and IV are represented separately as a Nalbuphine dimer ester, a Nalbuphine trimer ester and a Nalbuphine tetramer ester.

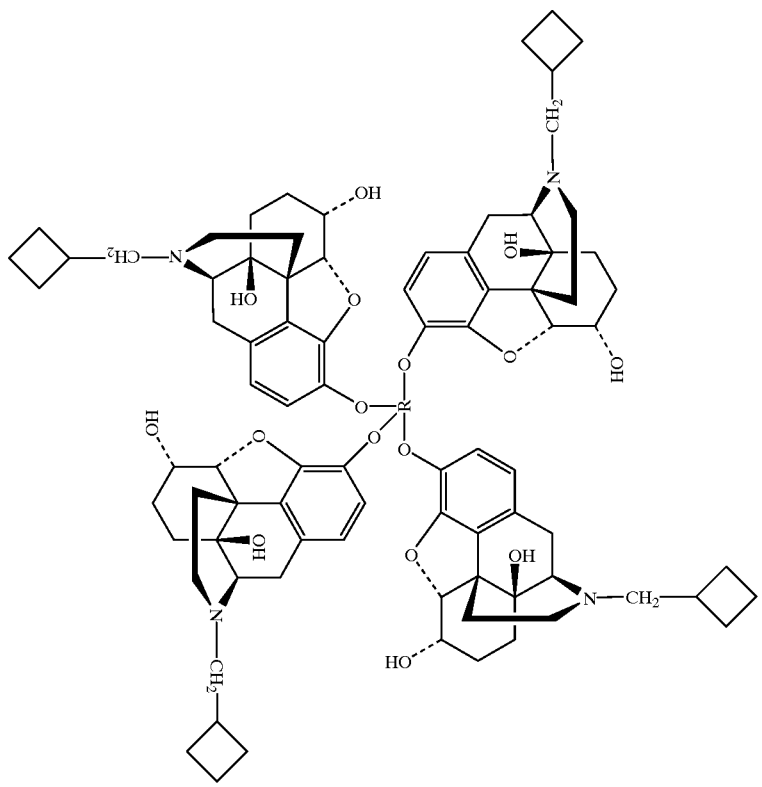

Formula IV

R is selected from a nonsaturated aliphatic fatty acid, or saturated aliphatic fatty acid; wherein R is also described by R'CO, the R' denotes the aliphatic group consisting of alkyl or alkylene having 1 to 40 carbon atoms. The aliphatic group is selected from (a) a straight alkyl group, (b) a branched alkyl group, (c) a straight alkyl group substituted with a benzene ring, (d) a branched alkyl group substituted with a benzene ring, (e) a benzenyl group where the benzene ring contains a straight chain aliphatic group and, (f) a benzenyl group where the benzene ring contains a branch chain of aliphatic group. In brief, when the ratio of Nalbuphine base group to ester group was 1:1, as shown in formula I, it was Nalbuphine monomer ester. When the ratio was 2:1, as shown in formula II, it was Nalbuphine dimer ester. When the ratio was 3:1, as shown in formula III, it was a Nalbuphine trimer ester. The Nalbuphine polyester derivatives are Nalbuphine dimer ester, Nalbuphine trimer ester, or Nalbuphine tetramer ester. When the R group was hydrogen and n is equal to 1, it represented Nalbuphine.

The synthesis of Nalbuphine polyester derivative is shown in FIG. 1. Through the B path, Nalbuphine hydrochloride was dissolved in dichlormethane then acid anhydrides or chlorides of fatty acids solution were added that had been mixed previously with triethylamine. The esterification of Nalbuphine chloride was carried out by reacting with an aliphatic saturated fatty acid, or nonsaturated aliphatic fatty acid. Upon completion of esterification, the product was purified by passing through a silica gel column, and Nalbuphine monomer ester with formula I was obtained. When 1 mole of Nalbuphine chloride was added continual esterification of Nalbuphine dimer ester with formula II was obtained. The same procedure was repeated several times for the compound with formula II in order to obtain the Nalbuphine trimer ester with formula III, or Nalbuphine tetramer ester with formula IV, which were the Nalbuphine polyester derivatives. Through the A path, 4 moles of Nalbuphine hydrochloride was dissolved in dichlormethane then acid anhydrides or chlorides of fatty acids solutionn were added that had been previously mixed with triethylamine Nalbuphine ester tetramer with formula IV was obtained. The same procedure was repeated forming several Nalbuphine polyester derivatives of the Nalbuphine trimer ester with formula III. The other preparation method could employ Nalbuphine hydrochloride as the starting material, followed by adding chloride to Nalbuphine, then esterification was achieved by adding acid anhydrides or fatty acid, which had different substituted aliphatic groups. The Nalbuphine polyester derivative with formula II~IV was isolated and purified.

Adequate reactants of the present invention which included propionic acid, n-valeric acid, pivalic acid, benzoic acid, enanthic acid, decanoic acid, and saturated fatty acids such as stearic acid, lauric acid, arachidic acid, cerotic acid, etc. Non-saturated fatty acids included linolenic acid, undecylenic acid, cinnamic acid, etc. In formula IV, the R group represents fatty acids with different alkyls or alkylenes having 1 to 40 carbon atoms. When R is R'CO, R' could represent a saturated or nonsaturated alphatic chain, with carbons from 1 to 40. The aliphatic chain is selected from (a) a straight alkyl group, (b) a branched alkyl group, (c) a straight alkyl group substituted with a benzene ring, (d) a branched alkyl group substituted with a benzene ring, (e) a benzenyl group where the benzene ring contains a straight chain aliphatic group, and (f) a benzenyl group where the benzene ring contains a branch chain of aliphatic group.

An alternative method for the preparation of Nalbuphine polyester derivative was shown in FIG. 1 through the C path, using Nalbuphine hydrochloride as the starting material, followed by adding 2-dipyridine carbonate and N,N-dimethylpyridine chloride to Nalbuphine. Then esterification was achieved by adding acid anhydrides or fatty acid, which had different substituted aliphatic groups. The Nalbuphine polyester derivative with formula II~IV was isolated and purified. In this method, Nalbuphine was reacted with saturated or nonsaturated fatty acid, 4-dimethylaminopyridine, N,N'-dicyclohexylcarbodiimide, to obtain Nalbuphine polyester derivatives (II~IV). Reagents such as 4-dimethyamino-pyridine could be replaced by HOBT or pyridine. The additional amounts of those reagents were required by the number of ester groups in product IV. Usually, the additional amounts were the module as nonsaturated aliphatic fatty acid, or saturated aliphatic fatty acid substituted with aliphatic alkyl or alkylene groups. However, additional amounts of reagents in the process of preparing Nalbuphine polyester derivative was regulated under the number of ester groups in the product. The additional amounts of reagents in the process of preparing Nalbuphine ester dimer was required to be two times the amount of the starting material. The additional amounts of 4-dimethylaminopyridine needed was less than 1%. In preparing Nalbuphine ester trimer three times were required. The additional amounts of 4-dimethylaminopyridine needed was less than 2%.

The synthesis of Nalbuphine polyester derivative was shown in FIG. 1. Nalbuphine was reacted with fatty acid chloroate, or aliphatic fatty acid halide to give Nalbuphine polyester derivative having formulae II~IV. In 1975, *JACS* volume 97, page 3515 even reported the use of Mg(OCOCF$_3$)$_2$ and alkaline reagents, or use halides in acids to react with Nalbuphine to give Nalbuphine esters. In 1981, *Synth. Comm.* volume 11, page 121 reported the use of 1-flouro-2,4,6-tri-nitrobenzene and N,N-dimethylaminopyridine to synthesize Nalbuphine ester. In 1983, *Bull. Chem. Soc.* Jpn. volume 56, page 639, aromatic Nalbuphine ester was prepared by mixing pyridine, 1-chloro-2,4-nitropyridine and an aromatic fatty acid. In 1984 *Tetraheder Lett.* volume 25, page 4943, reactants such as N,N-dimethylaminopyridine, di-2-pyridyl carbonate was used. However, these prepared methods only described the product of Nalbuphine monomer ester.

The process of preparing Nalbuphine polyester derivative in the invention was different from common ester compounds, especially regarding reaction conditions such as pH value and temperature. For product stability, the reaction conditions required controlling the pH value. The optimal pH was 8 to 10. Temperature also affected the yield of product, when it was at higher temperature the by-product was increased, on the other hand lower temperature caused incomplete esterification. The reaction occurred between −10° C. to 100° C., while the optimum temperature should be slightly below room temperature. When aromatic fatty acids were used, the temperature should be controlled between 0° C. to 80° C., and the optimum temperature was lower than the room temperature. When aromatic fatty acid halides were used, the temperature should be between −10° C. to 50° C., and the optimum temperature was lower than room temperature.

In the synthesis method, Nalbuphine was reacted with reagents as 4-dimethyaminopyridine could be replaced by HOBT or pyridine. The adding amount of those reagents was according to the number of ester groups in product(II~IV). Usually, the adding amount was 2 times, one time, 1%, or 2% of starting material. The adding amount of Nalbuphine base group was interrelated with the ester group of acid anhydrides, chlorides of fatty acids, or aliphatic fatty bi-acid that was influenced to the transfer ratio of final product. However, the adding amount ratio was 2:1, and the transfer ratio of Nalbuphine ester dimmer was 80%. The adding amount ratio was increased to 2.2:1, and the transfer ratio of Nalbuphine dimmer ester was raised to 85%. On the other hand, the adding amount ratio was 2:1.15, and the transfer ratio of Nalbuphine dimer ester was raised to 90%.

In order to increase the yield, the purification step in the synthesis method of the present invention employed multiple solvents and multiple stages. Those employed multiple solvents selected from polar solvents or nonpolar solvents. Some solvents are unfavorable for the process; one affected product stability such as water and methanol affected which are poor solvents for Nalbuphine polyester derivative, another affected yield and environmental pollution such as THF, hexane, and ether. Another was expensive such as dichloromethane and dichloroethane which slowed crystallization. In brief, multiple solvents were employed, such as ethanol and ethanol/propanol in the process.

Table 1 shows the physical characteristics of compounds of Nalbuphine polyester derivative obtained in the present invention which were analyzed by NMR, IR, UV, GC-MS. Those compounds were prepared to form various dosage forms for oral, topical route or parenteral administration such as intramuscular, intracerebroventricularly intravenous, and intrathecal.

Soft Drug Design Of Nalbuphine Polyester Derivative

The present invention adopted the design of a "soft drug". The item, soft drug, was different from prodrugs or hard drugs. Generally, hard drugs were the products that were prepared by the synthesis from starting materials, or purified from a natural product. Those hard drugs usually have some activity, and are combined with mineral toxicity. Via in vitro and in vivo tests, the active mechanism of hard drugs were studied in detail. A prodrug was designed under the dates of active mechanisms that were collected bypharmacokinetic and pharmacodynamic studies. Those prodrugs were metabolized in two parts; namely an activity part, and unknown part. For a Nalbuphine soft drug, it was necessary to know the active form of the drug (Nalbuphine) first, then a nontoxic-prodrug was synthesized from an active form of Nalbuphine with a non-active and nontoxic compound. As shown in FIG. 2, compound II, III and IV were Nalbuphine soft drugs, which would release bioactivity Nalbuphine in the animal body. Nalbuphine polyester derivative can be converted into Nalbuphine and a non-active and nontoxic metabolites by metabolism. Therefore, the Nalbuphine soft drug body was different from common Nalbuphine prodrugs or hard drugs. Since they were not converted into toxic metabolites, the design of soft drug was the safest way.

Properties of Nalbuphine Polyester Derivative

I. For Rat Experiments
  (a) Dinalbuphine sebacoyl ester(SDN) was dissolved in acetonitrile, the concentration was 7.75 mg/ml.
  (b) 250 ml of whole blood was collected from rats given dinalbuphine sebacoyl ester, and anticoagulant was added.

II. For Rabbit Experiments
  (a) Dinalbuphine ester sebacoyl ester was dissolved in acetonitrile, the concentration was 5.2 mg/ml.
  (b) 150 ml of whole blood collected from rats given dinalbuphine sebacoyl ester, and anticoagulant was added.

III. For Dog Experiments
  (a) Dinalbuphine sebacoyl ester was dissolved in acetonitrile, the concentration was 12.5 mg/ml.

(b) 200 ml of whole blood collected from rats given dinalbuphine sebacoyl ester, and anticoagulant was added.

IV. For Human Experiments (a) Dinalbuphine sebacoyl ester was dissolved in acetonitrile, the concentration was 10 mg/ml.

(b) 250 ml of whole blood collected from rats given dinalbuphine sebacoyl ester, and anticoagulant was added.

All blood collections were analyzed by HPLC, half-lives in various animals were shown in Table 2 and Table 3. For rats, the half life was 2.8 minutes, rabbits was 7.0 minutes, dogs was 27.8 minutes, and humans were 9.0 minutes. The converted time of 90% dinalbuphine sebacoyl ester(SDN) into Nalbuphine, for rats it was 10 minutes, rabbits were 25 minutes, dogs were 95 minutes, and 30 minutes for humans.

Long Acting Pharmaceutical Composition

In 1986, Gelders, Y. G. reported in *Int. Clin. Psychophacol.* volume 1, page 1, regarding Haloperidol decanoate as long acting prodrug for Haloperidol. Intramuscular parenteral administration was given, and the analgesic effect was extended from 2 to 4 times a day, to 1 to 2 times a month. In 1987, Norman T. R. reported in *Int. Clin. Psychopharmacol.* Volume 2, page 299–305, regarding the preparation of Fluphenazin decanoate from Fluphenazin. In 1988, Hinko, C. N. reported in *Neuropharmacology* volume 27, page 475 to 483, regarding the preparation of ester of Nipectic acid. In 1988, Broekkamp C. L. reported in *J. Pharm. Pharmacol.* volume 40, page 434 to 437, regarding the preparation of Nicotinoyl morphine ester from Morphine. Joshi, J. V. et al. reported in 1989, *Steroids*, volume 53, pages 751 to 761 regarding a precursor preparation of Northisterone enanthate, where the dosing can be set longer to two months.

In general, to maintain the therapeutic efficacy, various dosage forms were preparedbywhich drugs may utilize esterification, or are suspended in an oil vehicle to form parenteral suspension administration. When it is in the animal body, the release rate of those drugs may slow down, which is caused by factors such as increased solubility in fat or lesser blood flow. In these cases the dosing interval can be set longer. In 1986, Gelders reported in *Int. Clin. Psychophacol*, volume 1, page 1, and Hinko, C. N. et al. reported in *Neuropharmacology* volume 27, page 475, about adding co-solvents such as sesame oil or soybean oil to precursor Haloperidol decanoate to form controlled dosage forms. However, simply suspending the drug in the oil sometimes could achieve release quickly. For instance, Tanaka, T. reported in 1974 in Chem. Pharm. Bull. volume 22, page 1275 to 1284, about intramuscular administration of a Testosterone suspension that Testosterone released quickly was found. Another in 1990, Titulaer, H.A.C. reported in J. Pharm. Pharmacol. volume 42, page 810 to 813, that suspending artemisinin in parenteral oil make various dosage forms for intramuscular, intravenous, oral, and rectal administration. The drug was released promptly. In 1994, Zuidema, Z. et al. reported in *International J. of Pharmaceutics*, volume 105, page 189 to 207, about the rate and extent of dosage forms for parenteral administration are very erratic and variable. In general, any attempt to suspend drug in oil vehicle for the purpose of long acting dosage forms required the consideration of physical solubility, stability, and release rate from such vehicle.

It is provided by Zuidema, Z. et al. report (*International J. of Pharmaceutics*, 1994) and inventor study, that the pharmaceutical compositions which suspended or dissolved the analogous chemical structure of active ingredient dosage forms in oil vehicle, did not certainly achieve the long duration therapeutic effect. It required testify and study. The prior art disclosed some long acting pharmaceutical composition comprising active ingredients such as hormones or antipsychotic drugs compounds. Those chemical structures of the active ingredients mentioned in the prior art, are different from nalbuphine polyester derivative. Therefore, the prior art does not have any teaching about the present invention. The present invention took consideration of these factors and many obstacles were overcome to achieve the goal of extending the duration of action.

The present invention also provides long acting dosage form for Nalbuphine polyester derivative. It employed a method which adds Nalbuphine polyester derivative to injectable oil vehicle, or to phosphate buffer, with the addition of common excipients to form a controlled release dosage form. In the present invention, the injectable oil vehicles were selected from sesame oil, ethylester of peanut oil, or soybean oil. The common excipients were selected from methyl paraben, propyl paraben, BHA, BHT, cremophore EL, pluronic, solutol, or span.

A few problems about the process of long acting dosage forms needed to be overcome. When dispersing of Nalbuphine polyester derivative in oil vehicle could cause precipitation, crystal or turbidity, the temperature was raised. The other problem was the total amount of active ingredient dissolved was low. Usually, the addition of some surface as excipient, the total amount of Nalbuphine polyester derivative was low such as only 8.5%, 16.8%, still far away from 95%. Therefore, the strategy of using multiple excipients, or raised temperature was adopted on the process. The result was not satisfactory, although the total amount of Nalbuphine polyester derivative was increased, some one far away from 95%, others over 95% but unfit for parenteral administration.

As shown in Table 4, favorable excipients that form long acting dosage forms of Nalbuphine polyester derivative was listed. One or more then one excipients were selected from methyl paraben, propyl paraben, benzyl alcohol, and span. Those excipients can solve the problems between Nalbuphine polyester derivative and the oil vehicle such as precipitation, crystal or turbidity. The Table 5 shows that the amounts of excipients were between 0.01 to 46%, and the total amount of Nalbuphine polyester derivative dissolved was more than 95%.

The pharmaceutical composition comprising Nalbuphine polyester derivative in the present invention were tested in animals such dogs, and Sprague Dawley rats for analgesic effect by intramuscular, intravenous parenteral administration. A phosphate buffer containing the same amount of drug was used for the control group.

Selection Of Injectable Oil Vehicle For Controlled Release Dosage Form (1) Materials Sesame oil (Sigma, Mo., USA), soybean oil (Sigma, Mo., USA), peanut oil (Chun Sin, Taipei, Taiwan) were tested in the present invention as the oil vehicle for Nalbuphine polyester derivative. Phosphate buffer was prepared by adding 1.9 g of monobasic potassiumphosphate, 8.1 g of dibasic sodium phosphate, 4.1 g of sodium chloride to 1 liter of water to make isotonic buffer solution of pH 7.4 and used as a control group.

(2) Experimental

Each experimental group has 6 samples. Into a dialysis bag were placed 50 mg(0.127 mmole) of Nalbuphine hydrochloride, or 45 mg Nalbuphine free base(0.127 mmole) was added in 1 ml previous mentioned oil vehicle or phosphate buffer. Then the solution was filled into a dialysis bag. The cut off for the dialysis bag was 12,000–14,000 molecular weight. A 250 ml of an iodine flask containing 150 ml of phosphate buffer was used to place into the dialysis bag. Inside the flask, a magnetic stirring bar(Fargo, Taipei, ROC) was placed. The dialysis proceeded at stirring speed of 500 rpm and the release rate of Nalbuphine from each preparation was measured. A UV spectrophotometer (Shimadzu, Kyoto, Japan) was used to detect the Nalbuphine content in the phosphate buffer outside the bag.

(3) Result

Figure 3:
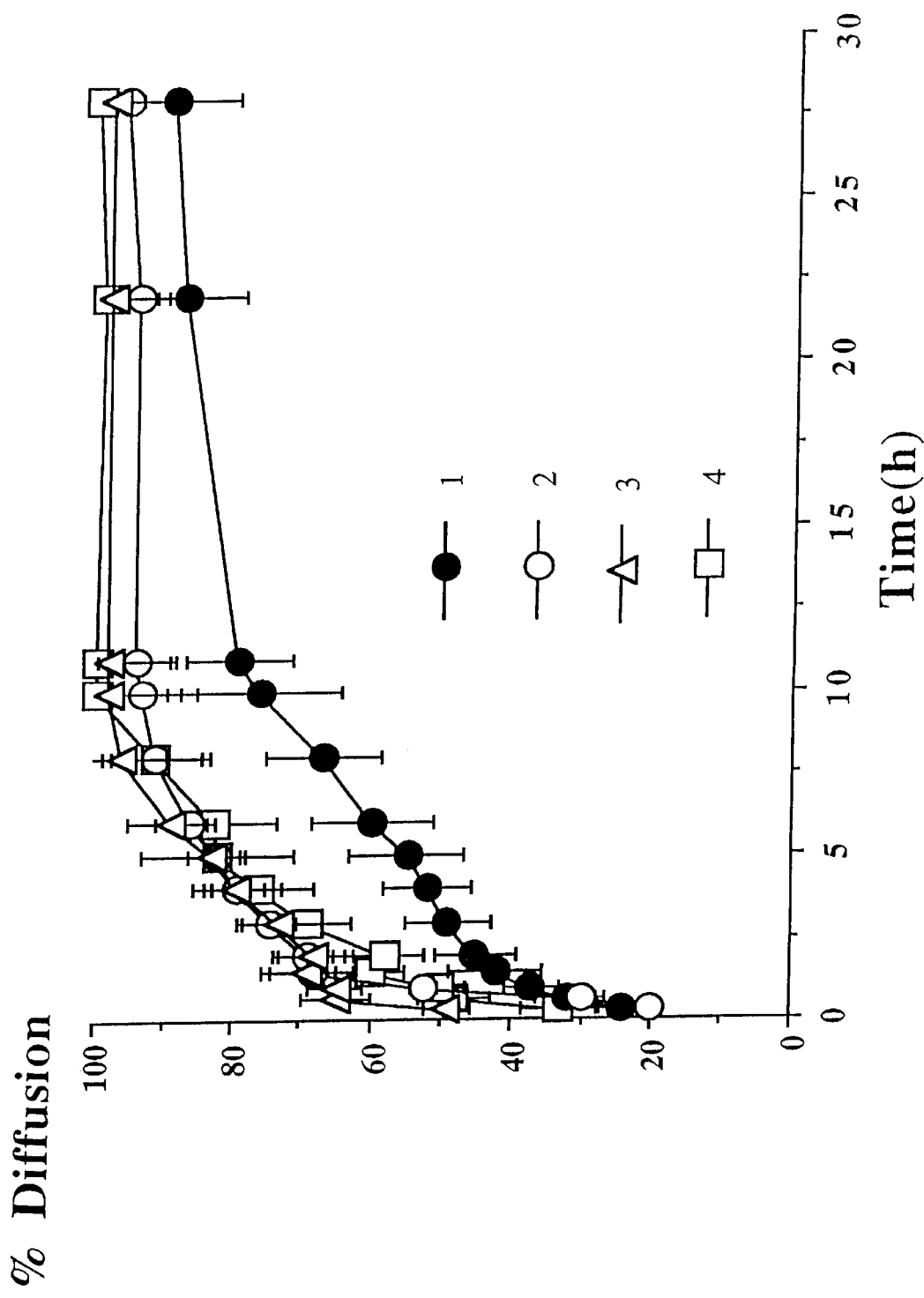
FIG. 3 depicts In vitro release of Nalbuphine hydrochloride from vehicles (average±standard deviation, n=6).
Figure 4:
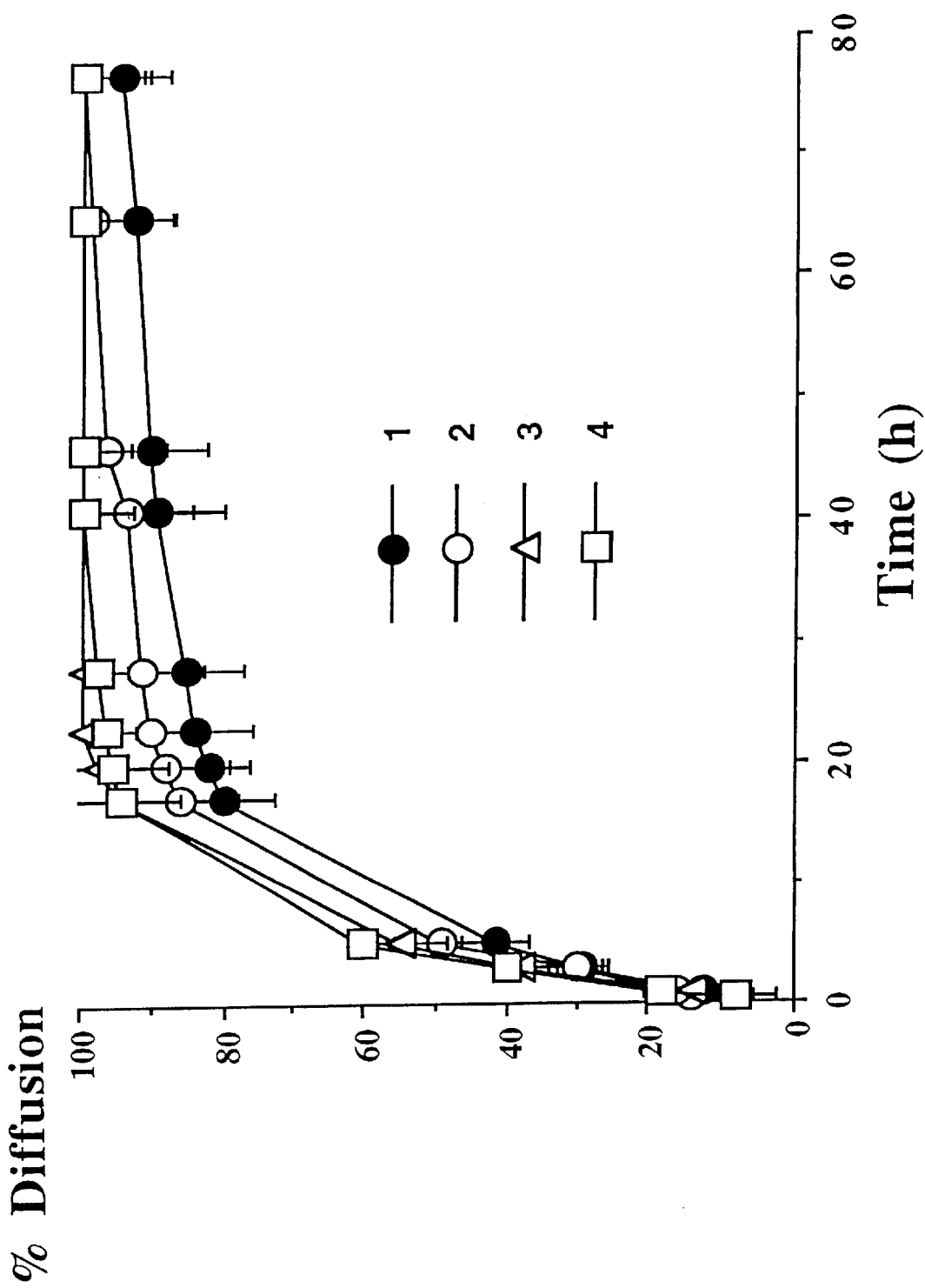
FIG. 4 depicts In vitro release of Nalbuphine freebase from vehicles(average±standard deviation, n=6).

The release profile of Nalbuphine from each preparation and control group(oil vehicle) were listed in FIGS. 3 and 4. As shown in FIG. 3 the preparation with sesame oil as the vehicle has the slowest release rate (p<0.05) and there is no significant difference within the other three preparations after a period of between 1 and 11 hours. FIG. 3 also shows that the amount of released Nalbuphine free base was less in the preparation with sesame oil than with peanut oil ester and the control between 17 and 28 hours (p<0.05).

FIG. 4 shown the amount of Nalbuphine released from preparation(A)Nalbuphine hydrochloride dissolved in sesame oil, preparation(B)Nalbuphine hydrochloride dissolved in phosphate buffer, and preparation(C)Nalbuphine free base dissolved in sesame oil. After 3 hours, the release in (B) is greater than (A) and (A) is greater than (C). After a period of between 3 and 28 hours (A) is greater than (C).

Pharmacodynamic Study For Long Acting Preparation Of Nalbuphine Monomer Ester

1) Animal

Sprague Dawley rats(175 to 225 g) were used. Each group consisted of 6 rats and each rats was injected once intramuscularly on the rear leg.

(2) Material

A. Dose response curve for analgesic effect (a) Nalbuphine hydrochloride, doses of 100 mg/kg, 10 mg/kg, 1 mg/kg, 0.5 mg/kg, 0.1 mg/kg, 0.05 mg/kg, 0.01 mg/kg were used.

(b) Morphine hydrochloride, doses were 10 mg/kg, 5 mg/kg, 1 mg/kg, 0.5 mg/kg, 0.1 mg/kg, 0.05 mg/kg, 0.01 mg/kg were used.

(c) Buprenorphine hydrochloride, doses were 100 mg/kg, 10 mg/kg, 5 mg/kg, 1 mg/kg, 0.5 mg/kg, 0.1 mg/kg, 0.01 mg/kg were used.

B. Pharmacodynamic study for Nalbuphine monomer ester (a) 25 micromole/2.8 ml of Nalbuphine hydrochloride in saline and 25 micromole/2.8 ml of Nalbuphine base in sesame oil were used as control groups. The dose for each rat was 25 micromole per kg, intramuscularly.

(b) 25 micromole/2.8 ml of Nalbuphine monomer ester ester such as propionate, enanthate, pivalate, benzoate, decanoate was dissolved and was used to form controlled release dosage forms. The dose for each rat was 25 micromole per kg, intramuscularly.

(3) Experimental

In the experiment, a circulating cold ethanol bath with a temperature maintained at −20° C. was set up. After dosing, the rat tail(⅓ from the tip) was immersed in the bath. The latency for the rat to flick its tail from the bath was measured to be the nociceptive threshold. The effect of various opium alkaloid preparations can be determined with this test.

The nociceptive effect can be calculated as follows:

$$\text{The percentage of nociceptive effect} = \frac{\text{The latency after dosing} - \text{The latency before dosing}}{\text{The latency experimental end} - \text{The latency after dosing}} \times 100$$

35, 25, 15 minutes before dosing, Male Sprague Dawley rat(175–225 g) was tested to measure the basic response latency. The time to top the experiment was set at 40 seconds to prevent the tail from cold sore. No cold sore were found in 40 sec. Five minutes after the drug was given to the rat, the flick test was performed every 10 minutes or more.

(4) Result

A. Dose response curve

Figure 5:
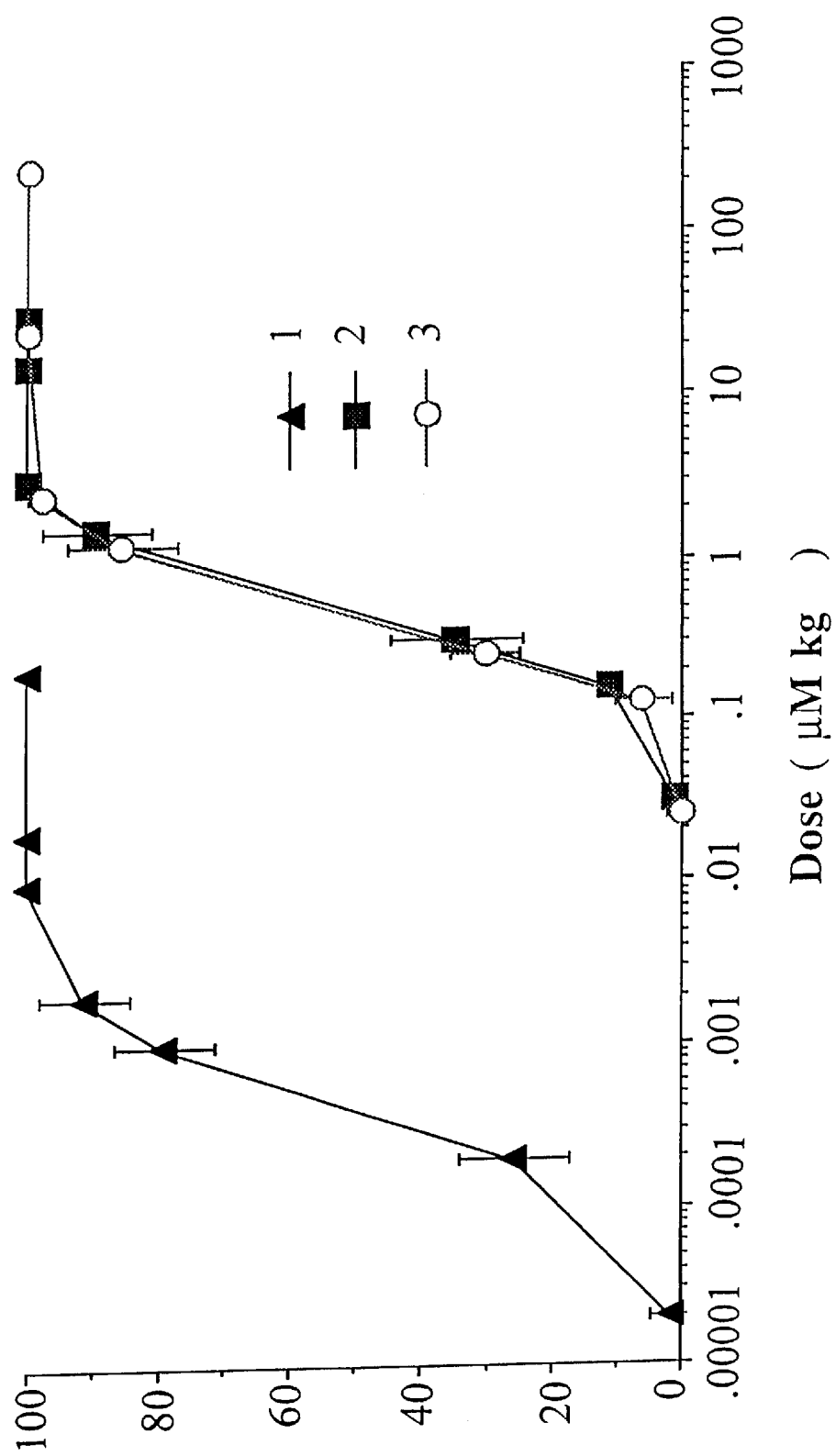
FIG. 5 depicts the analgesic effect of Nalbuphine HCl, Morphine HCl and Buprenorphine HCl.

The maximal analgesic effect for intramuscularly injection was found at 0.05 to 10 mg/kg for Morphine hydrochloride, 0.1 to 100 mg/Kg for Nalbuphine hydrochloride, 0.1 to 100 µg/kg for Buprenorphine. The dose response curve was shown in FIG. 5.

B. Pharmacodynamic study

Figure 6:
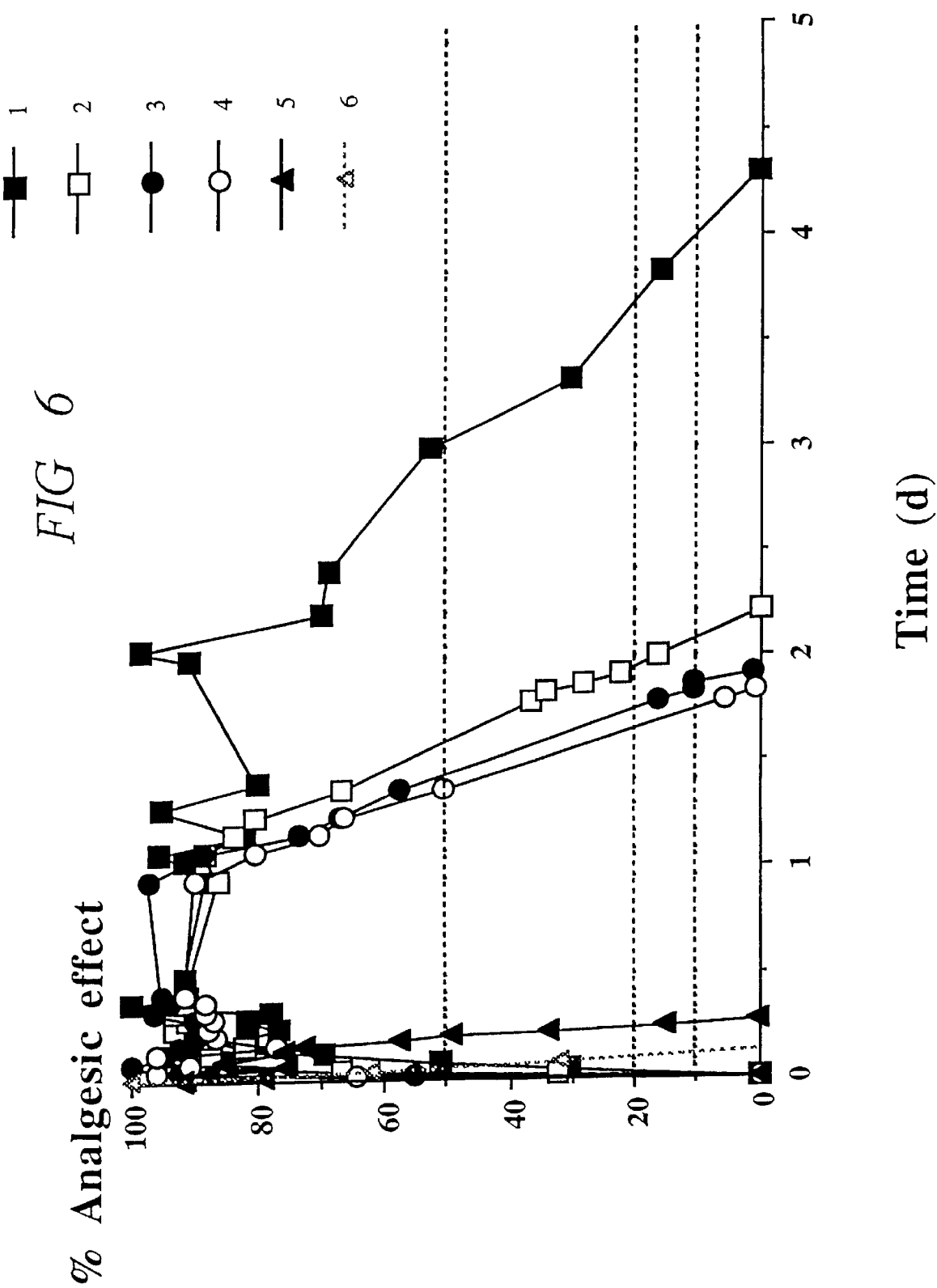
FIG. 6 depicts the analgesic effect after intramuscular injection of several nalbuphine monoester to rats (n=6).

FIG. 6 shows the analgesic duration of Nalbuphine free base was significantly shorter than from preparation of Nalbuphine monomer ester such as propionate, enanthate, pivalate, benzoate, decanoate.

Pharmacodynamic Study For Long Acting Preparation Of Nalbuphine Polyester Derivative (1) Animal Six male Sprague Dawley rats (175 to 225 g), and six male guinea pigs (200 to 250 g) were used.

(2) Material (a) Nalbuphine hydrochloride, dose for rats was 15.625 µM/kg, 62.5 µM/kg, 250 µM/kg. Dose for guinea pig was 500 µ/kg, 250 µM/kg.

(b) Nalbuphine hydrochloride parenteral dosage forms, Nalbuphine hydrochloride was dissolved in 0.9% normal saline.

(c) Dinalbuphine sebacoyl ester, dose was 7.8125 µ/kg, 31.25 µM/kg, 125 µM/kg.

(d) 50 mg/ml dinalbuphine sebacoyl ester parenteral dosage forms, dinalbuphine sebacoyl ester was prepared in sesame oil.

(3) Result

Figure 7:
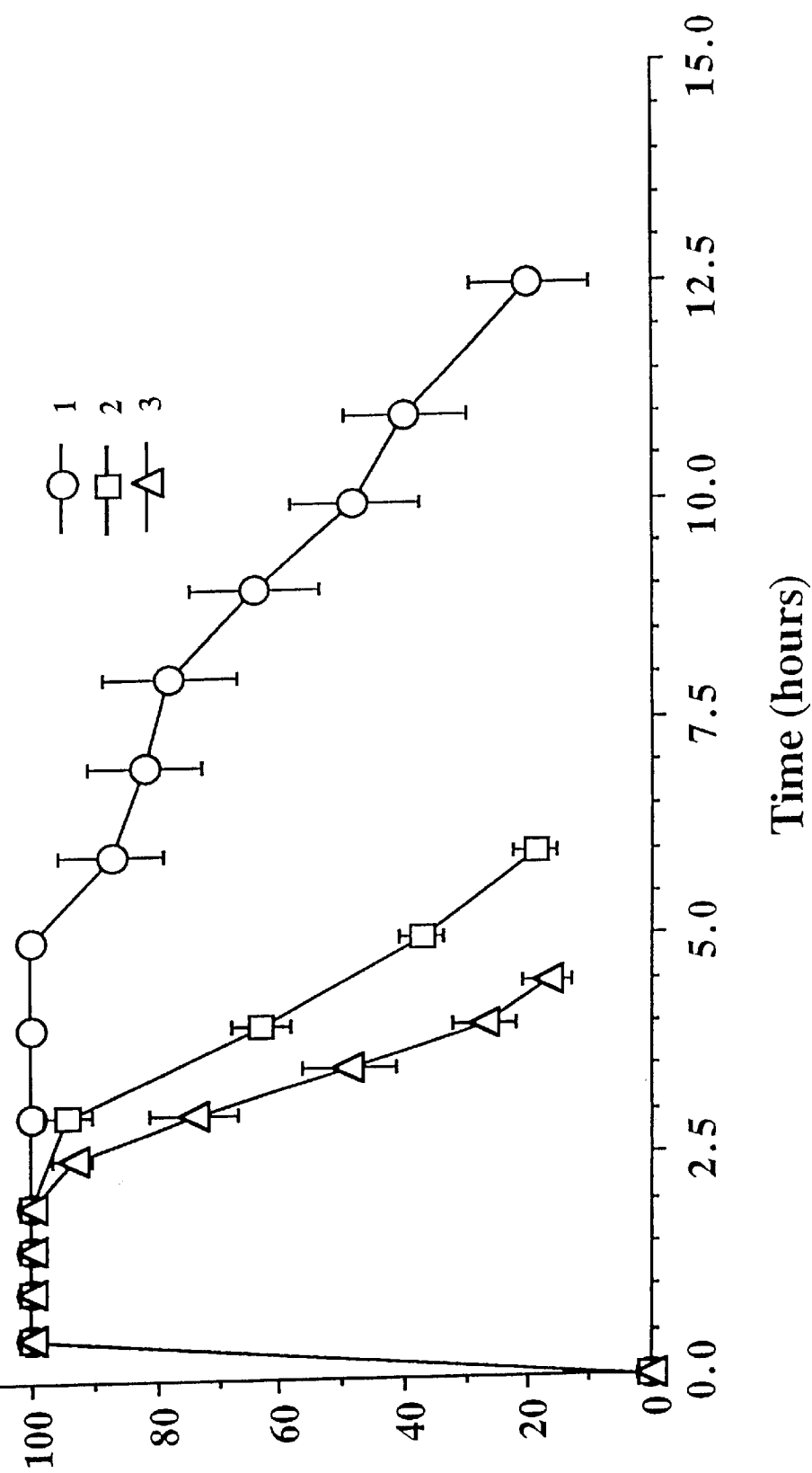
FIG. 7 depicts the analgesic effect after intramuscular injection of Nalbuphine HCl to rats.
Figure 8:
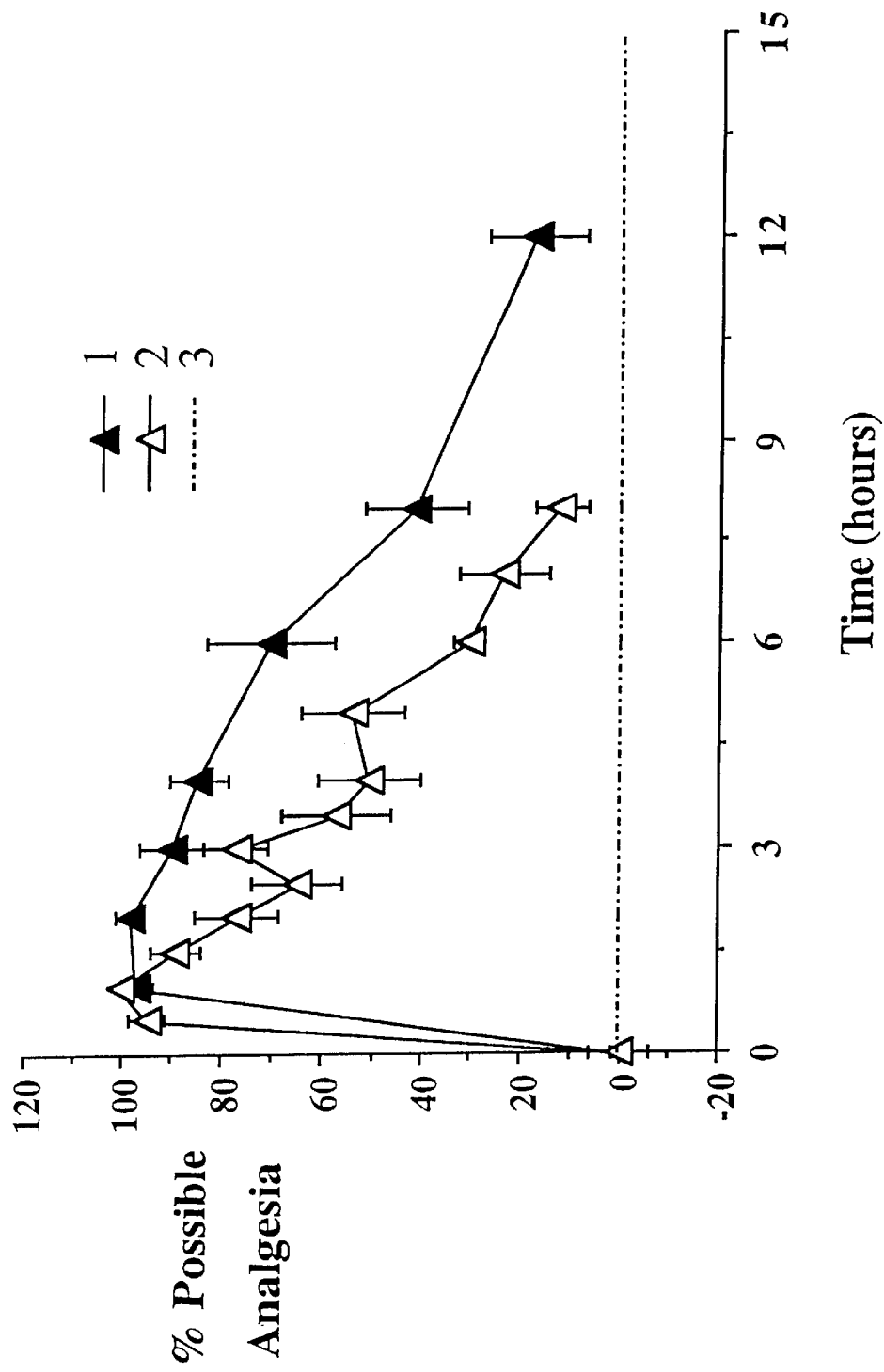
FIG. 8 depicts the analgesic effect after intramuscular injection of Nalbuphine HCl to Guinea pigs.
Figure 9:
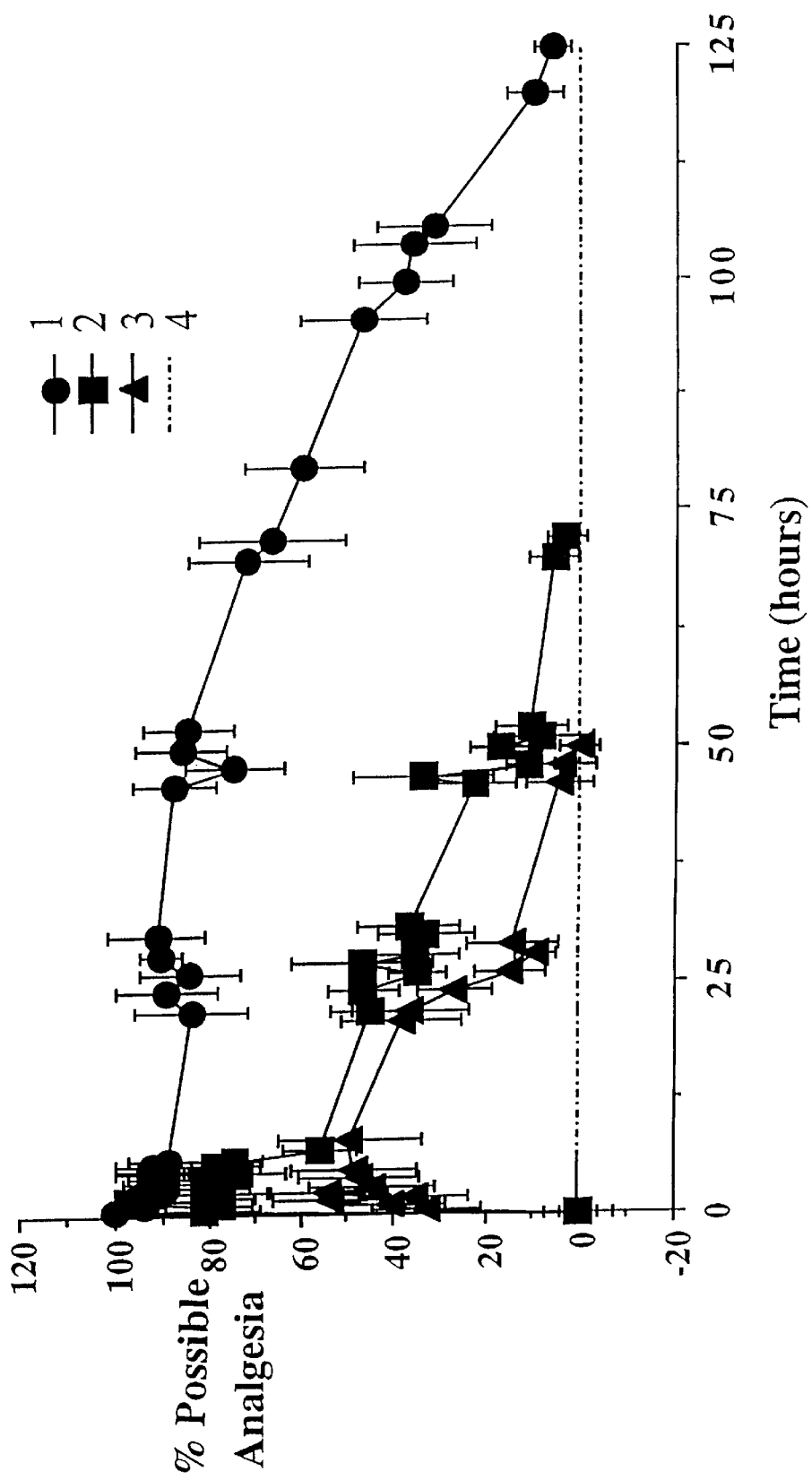
FIG. 9 depicts the analgesic effect after intramuscular injection of long acting sebacoyl dinalbuphine(SDN) to rats.

As shown in FIGS. 7 and 8, the significant analgesic effect for intramuscular injection was found at 15.625, 62.5, 250 µM/kg for rats and 500 µM/kg and 250 µM/kg for guinea pigs for Nalbuphine hydrochloride. As shown in FIG. 9, the significant analgesic effect was proportional to the dose administered for intramuscular injection and was found at 7.8125 µM/kg, 31.25 µM/kg, 125 µM/kg for rat for sebacoyl dinalbuphine. The analgesic effect was extended to 4–5 days, when the dose administered was below 125 µM/kg. For clinical experience, the analgesic effect maintained 4 to 5 days for intramuscular injection was found at 20 mg/65 kg (0.308 mg/kg) dose of Nalbuphine hydrochloride that was reported by Schmidt, W. K. et al (Drug Alcohol Depend. 14, 339, 1985). While the same level of analgesic effect for intramuscular injection was required at 15.625 µM/kg(6.165 mg/kg) to rats for 1:20 Nalbuphine HCl.

Figure 10:
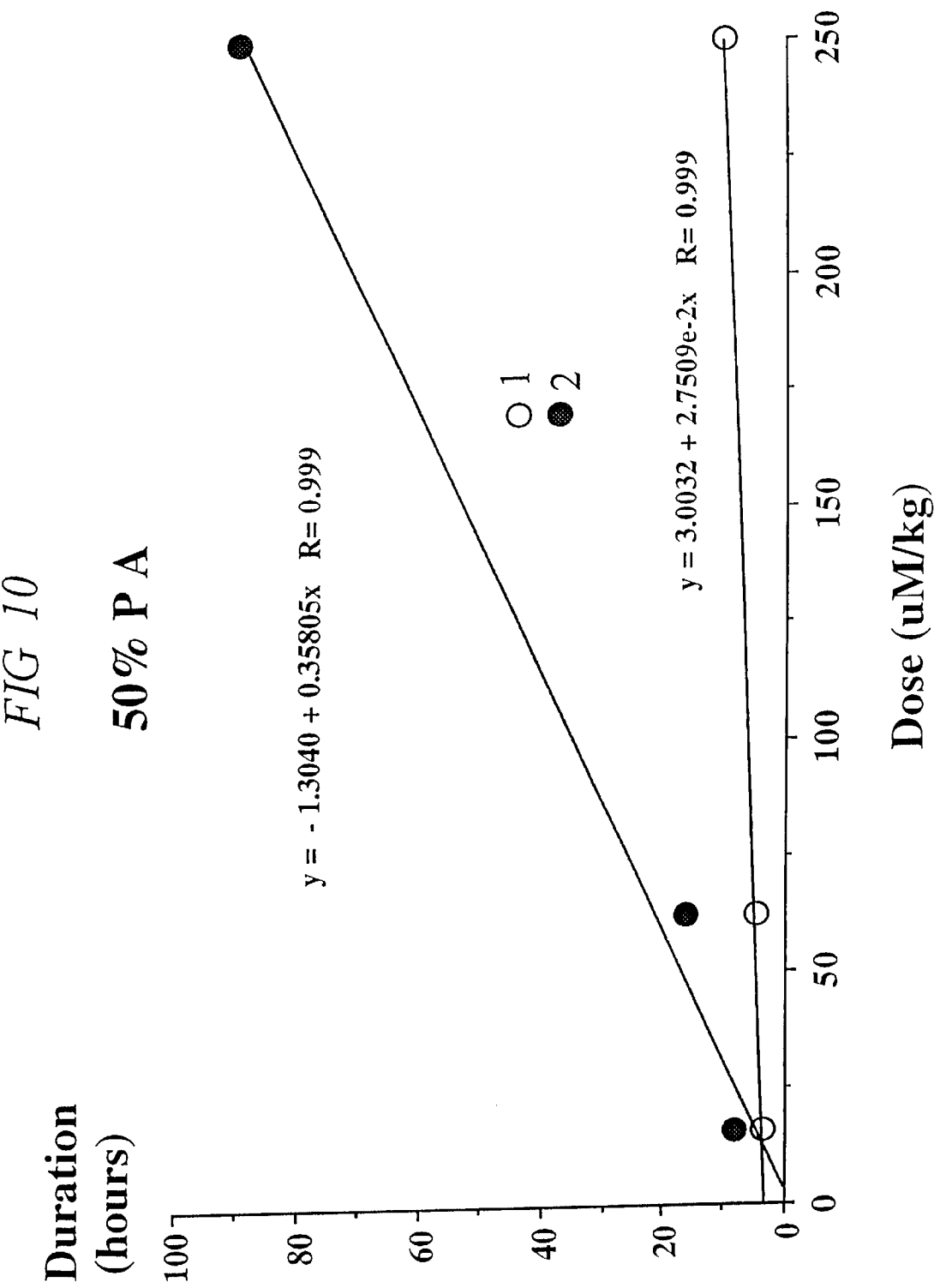
FIG. 10 depicts the dose response after intramuscular injection of long acting sebacoyl dinalbuphine(SDN) to rats.

As shown in FIG. 10, the 50% analgesic effect was extended to 88 hours for intramuscular injection of 125 µM/kg of sebacoyl dinalbuphine. The analgesic effect of sebacoyl dinalbuphine was 8.8 times of Nalbuphine hydrochloride. Therefore, the analgesic effect could be calculated on 4–5 days at 125 µM/23 kg to human body for sebacoyl dinalbuphine.

On clinic the analgesic effect was extended 4 to 5 hours for a single dose of an intramuscular injection at 20 mg/65 mg(0.308 mg/kg) of Nalbuphine hydrochloride. For the lipophilic solubility character of 20 mg Nalbuphine hydrochloride, the amount of injection was below 10 ml. For this reason, the analgesic effect could not be maintained 4 to 5 days even upon administration of 88 ml of Nalbuphine hydrochloride through metabolism. Besides, such parenteral volume was not ideal for a single dose. However, this invention made a development. By diluting a single dose of sebacoyl dinalbuphine in 7.15 ml sesame oil form, parenteral administration could give the analgesic effect maintained 4 to 5 days. In other words, the analgesic effect was extended 4 to 5 hours for a single dose of intramuscularly injected sebacoyl dinalbuphine at only 7 ml oil vehicle. This was owing to multiple steps of release for Nalbuphine polyester derivative, and such effect was adequate enough for the treatment of acute and chronic pain.

Pharmacokinetic Study For Long Acting Preparation Of Nalbuphine Polyester Derivative In Beagle Dog (a) Method Six Beagle dogs were used. Five Beagle dogs were intramuscularly injected with 30 mg/kg long acting sebacoyl dinalbuphine ester parenteral administration respectively, and another one was injection with 100 mg/kg long acting sebacoyl dinalbuphine ester oily parenteral administration. Blood samples were collected through the vein in front limb of dogs at 1, 2, 6, 24, 30, 48, 54, 72, 78, 96, 102, 120, 168, 192 hours. The concentrations of Nalbuphine and sebacoyl dinalbuphine ester in plasma were determined. Relationship between time and concentration was analyzed by PCNONLIN computer program. Two compartment model and pharmacokinetic parameters were calculated to depicted absorption, distribution, metabolism, and excretion of drugs in dogs.

(b) Result

Figure 11:
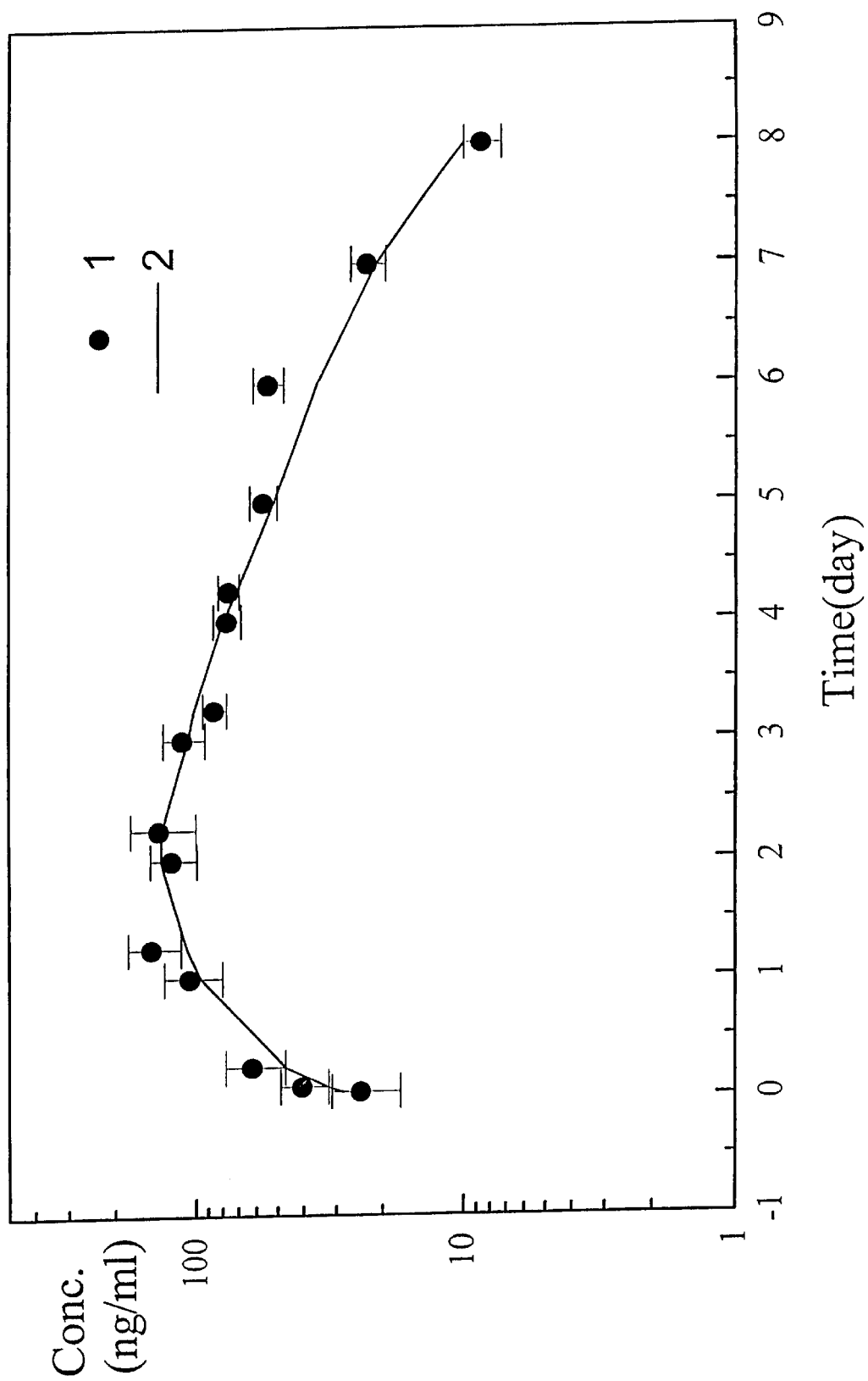
FIG. 11 depicts the plasma concentration of Nalbuphine after intramuscular injection of long acting sebacoyl dinalbuphine(SDN) 30 mg/k g to rats.
Figure 12:
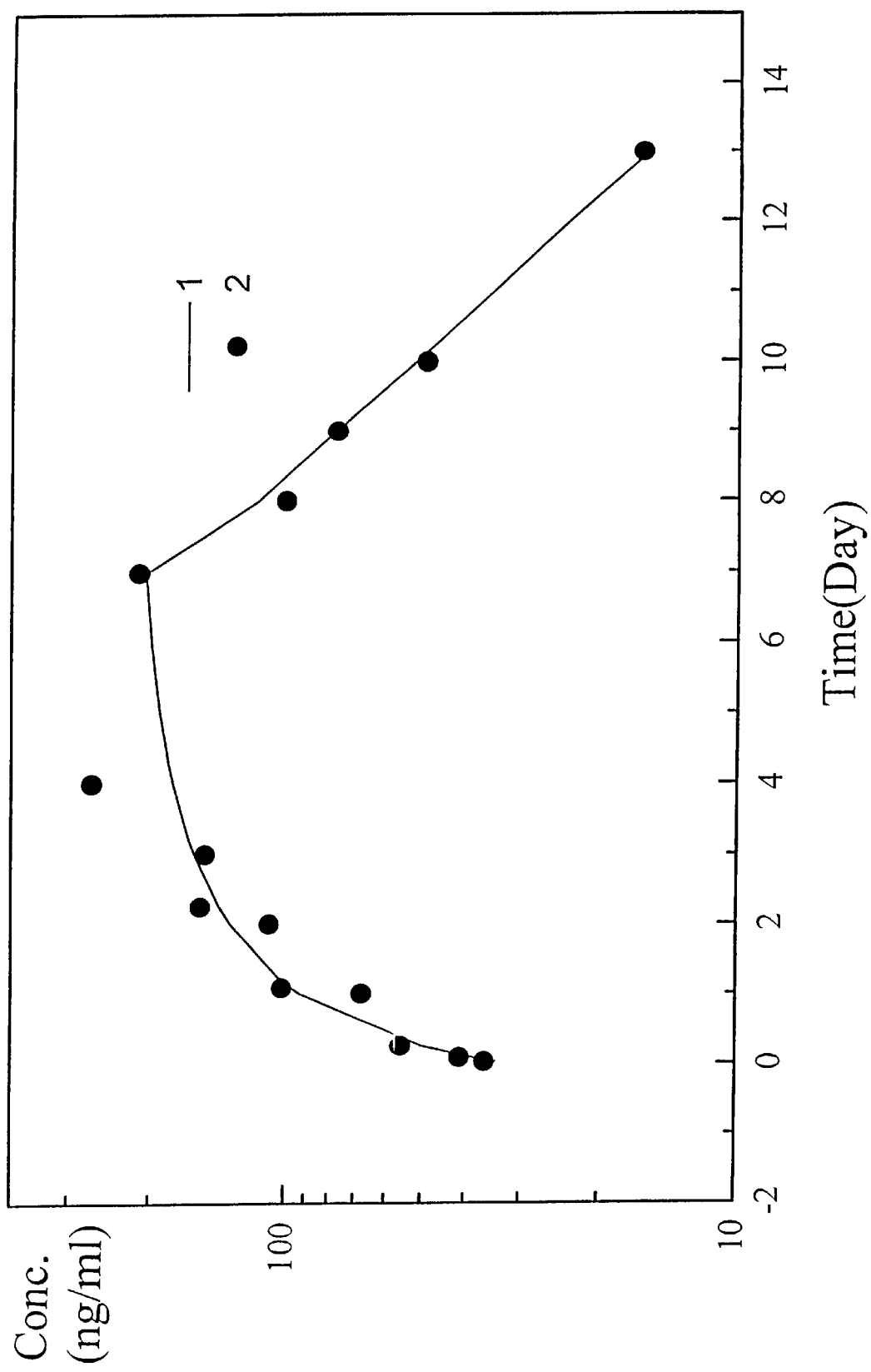
FIG. 12 depicts the plasma concentration of Nalbuphine after intramuscular injection of 30 mg/kg long acting sebacoyl dinalbuphine(SDN) to rats.

As shown in FIG. 11 and FIG. 12, the absorption of sebacoyl dinalbuphine ester in injection oil vehicle was presented as zero order. As dose was increased, the absorption time also increased and analgesics therapeutic efficacy exhibits longer duration. The distribution of sebacoyl dinalbuphine ester in animal was best fitted with a two compartment model. As shown in Table 6, the half life for excretion was about 30 hours. It was much longer than that of Nalbuphine hydrochloride, which was about 1 hour. However, this invention provides the long acting preparations of pharmaceutical composition comprising the Nalbuphine polyester derivative, which has longer analgesic effect than traditional preparations of Nalbuphine hydrochloride.

Besides, the bioavailability of sebacoyl dinalbuphine ester was about 63%. Data in Table 7 compared with Table 6, showed similar AUC/Dose and similar total clearance by two different dose administration as the same dog was tested, and showed similar AUC/Dose and similar total clearance. Thus, sebacoyl dinalbuphine ester presented a linear kinetic. This indicated that the dose of sebacoyl dinalbuphine ester increased, the zero order absorption rate also increased proportionally, and duration was also proportionally increased.

EXAMPLES

Example 1

Preparation of Nalbuphine propionate 75 ml of methylene chloride and 3.57 g(0.01 mole) of Nalbuphine were added to a 250 ml round-bottomed flask. The flask was placed in an ice bath to keep it cool. The content was stirred then gradually 0.16 mole of triethylamine was added. With rapid stirring, another 20 ml of dichloromethane solution containing 0.011 mole of propionic anhydride was added drop by drop. Afterward, the mixture was stirred at room temperature for 1 hour. 20 ml of 10% sodium carbonate solution was added to neutralize the residual acid and remove the water soluble impurities. Sodium sulfate was used to dehydrate the solution. After drying under vacuum, a Nalbuphine propionate solid was obtained. The product was purified by column chromatography.

Example 2 to 8

Preparation of Nalbuphine esters

Procedures in example 1 were followed, and as shown in Table 8, the different esters of Nalbuphine were obtained.

Example 9

Preparation of adipoyl dinalbuphine ester 5 g of Nalbuphine hydrochloride and 20 ml of dried dichloromethane were added into a round flask. The flask was placed in an ice bath. After 5 minutes, the content was stirred for 5 minutes then gradually 4.4 ml of triethylamine was added. Another 5 ml of dichloromethane solution containing adipoyl chloride was added drop by drop, then reacted for 30 minutes. Then the flask was removed from the ice bath to room temperature, and kept stirring for another 30 minutes, followed by filtration to remove salts. The filtrate was added with 10 ml of dichloromethane, then washed to 10 ml of saturated saline, followed by adding 10 ml of 5% citric acid solution. Magnesium sulfate was used to dehydrate the solution and to concentrate the organic layer. The white product was recrystallized in ethyl acetate and propanol. Finally 4.2 g of adipoyl dinalbuphine ester was obtained. The melting point was determined to be 78 to 79° C.

Example 10 to 14

Preparation of other dinalbuphine esters

Other esters of dinalbuphine esters listed in table 8 were prepared by following procedures in example 9.

Example 15

Preparation of sebacoyl dinalbuphine ester (method I)

20.2 g of sebacoyl acid and 200 ml of dimethylamine were added into a round flask. The flask was placed in an ice bath. After 5 minutes, the content was stirred for 30 minutes then gradually 32.4 g of 2-dipyridine carbonate was added. 5 g of N, N-dimethylpyridine and 78.8 g of Nalbuphine hydrochloride was added then reacted for 30 minutes. Then the flask was removed from the ice bath to room temperature, and kept stirring for 18 hours, followed by filtration to remove salts. When reaction was done, acetic acid was added to neutralize the filtrate to pH 7. Then the solution was evaporated to remove dimethylamine. Upon removal, 500 ml of dichlormethane was added, followed by washing with 20 ml of saturated sodium chloride solution 3 times, and 20 ml of 5% citric acid 2 times. Magnesium sulfate was used to dehydrate the solution and to concentrate the organic layer. The yellowish solid was recrystallized in acetyl acetate and n-hexane. Finally 50.2 g of sebacoyl dinalbuphine ester was obtained.

Example 16

Preparation of sebacoyl dinalbuphine ester (method II)

1.84 g octanoic acid and 5 ml of dichloromethane was added to a round flask. 3.93 g of Nalbuphine hydrochloride and triethylamine was put into flask. The flask was placed in an ice bath. Then stirred for 30 minutes for reaction at room temperature. Then the flask was placed in an ice bath for 5 minutes. Upon the formation of salt, the mixture was filtered, the dichloromethane solution was concentrated, and 5 ml of 10%l sodium bicarbonate was added to dissolve oily stuff. Then the pH of the solution was adjusted to 2.0 with 5 N HCl to allow sebacoyl dinalbuphine ester to precipitate. The precipitate was put into a round flask, dissolved then with 5 ml of dimethylamine. The flask was placed in an ice bath. Then 2.16 g of 2-dipyridine carbonate, 3.93 g of Nalbuphine hydrochloride, and 1 g of N,N dimethylpyridine were mixed in the ice bath and kept stirring for 30 minutes. The reaction was allowed at room temperature for 18 hours. Then the reaction solution was moved by filtration on ice bath for 5 minutes. The solution was dried subsequently, followed by adding 20 ml of dichloromethane and washing with 10 ml of saturated sodium chloride solution 3 times. Then 10 ml of 5% citric acid was added to wash twice. Magnesium sulfate was used to dehydrate the solution and to concentrate the organic layer. The yellowish solid was recrystallized in acetyl acetate and n-propanol. Finally sebacoyl dinalbuphine ester was obtained.

Example 17
Preparation of 1,3-cyclohexane diacid dinalbuphine ester 2 g of Nalbuphine hydrochloride and 10 ml of dichloromethane was added into a round flask. The flask were placed in an ice bath. After 5 minutes, The content was stirred then gradually 1.76 ml of triethylamine was added. With rapid stirring, another 5 ml of dichloromethane solution containing 0.53 g of 1,3 cyclohexane diacid chloride was added drop by drop. Upon reaction for 30 minutes, the flask was moved from the ice bath to room temperature and the reaction was continued for another 30 minutes. The reaction was stopped in an ice bath for 5 minutes. Upon the formation of salt, the mixture was filtered to remove salts, the filtrate was added to 20 ml of dichloromethane, followed by washing with 20 ml of saturated sodium chloride 3 times, and 20 ml of 5% citric acid twice. Magnesium sulfate was used to dehydrate the solution and to concentrate the organic layer. Subsequently a white solid was purified by column chromatography to give product. The molecular formula was determined to be $C_{50}H_{62}N_2O_{10}$ for 1,3 cyclohexane diacid dinalbuphine ester.

Example 18
Preparation of Docosanodic dinalbuphine ester 2 g of Nalbuphine hydrochloride and 10 ml of dichloromethane were added into a round flask. The flask was placed in an ice bath. After 5 minutes, 1.76 ml of triethylamine and 5 ml of dichloromethane solution containing 1.03 g of docosanodic diacid chloride were added drop by drop. Upon reaction for 30 minutes, the flask was moved from the ice bath to room temperature and the reaction continued for another 30 minutes. The reaction was stopped in an ice bath for 5 minutes. Upon the formation of salt, the mixture was filtered to remove salts, the filtratre was added to 20 ml of dichloromethane, followed by washing with 20 ml of saturated sodium chloride 3 times, and 20 ml of 5% citric acid twice. Magnesium sulfate was used to dehydrate the solution and to concentrate the organic layer. Subsequently a white solid was purified by column chromatography to give product. The molecular formula was determined to be $C_{64}H_{92}N_2O_{10}$, and the molecular weight determined to be 1048.92 for docosanoidic dinalbuphine ester.

Example 19
Preparation of 3,3-dimethylglutaric diacid dinalbuphine ester 2 g of Nalbuphine hydrochloride and 10 ml of dichloromethane were added into a round flask. The flask was placed in an ice bath. After 5 minutes, 1.76 ml of triethylamine and 5 ml of dichloromethane solution containing 0.5 g of 3,3 dimethylglutaric acid chloride were added drop by drop. Upon reaction for 30 minutes, the flask was moved from the ice bath to room temperature and the reaction continued for another 30 minutes. The reaction was stopped in an ice bath for 5 minutes. Upon the formation of salt, the mixture was filtered to remove salts, the filtrate was added with 20 ml of dichloromethane, followed by washing to 20 ml of saturated sodium chloride 3 times, and 20 ml of 5% citric acid twice. Magnesium sulfate was used to dehydrate the solution and to concentrate the organic layer. Subsequently a white solid was purified by column chromatography to give product. The molecular formula was determined to be $C_{49}H_{62}N_2O_{10}$, and the molecular weight determined to be 839.04 for 3,3 dimethylglutaric dinalbuphine ester.

Example 20
Preparation of trinalbuphine trimesoyl ester (method I)

5 g of Nalbuphine hydrochloride and 20 ml of dichloromethane were added into a round flask. The flask was placed in an ice bath. After 5 minutes, 4.4 ml of triethylamine and 5 ml of dichloromethane solution containing 1.12 g of trimesoyl chloride were added respectively. Upon reaction for 30 minutes, the flask was moved from the ice bath to room temperature and stirred for another 30 minutes. The reaction was stopped in an ice bath for 5 minutes. Upon the formation of salt, the mixture was filtered to remove salts, the filtrate was added with 20 ml of dichloromethane, followed by washing to 20 ml of saturated sodium chloride 3 times, and 10 ml of 5% citric acid twice. Magnesium sulfate was used to dehydrate the solution and to concentrate the organic layer. Subsequently a white solid was purified by column chromatography to give product. The solid was recrystallized in n-hexane. The yield of trinalbuphine trimesoyl ester was 4.5 gm, and the formula was determined to be $C_{50}H_{56}N_2O_{10}$.

Example 21
Preparation of trinalbuphine trimesoyl ester (method II)

18.6 g of trimesoyl acid and 150 ml of dichloromethane was added to a round bottom flask. After 5 minutes, 20.3 g of 1-chloro-2,4-nitropyridine and 9.9 g of pyridine were added and kept stirring for 30 minutes. With rapid stirring, 118.05 g of Nalbuphine hydrochloride was added. Then the flask was moved from the ice bath to room temperature and the reaction continued for 18 hours. Upon the formation of salt, the mixture was filtered to remove salts, the filtrate was added with 200 ml of dichloromethane, followed by washing to 20 ml of saturated sodium chloride 4 times, 20 ml of 5% citric acid 3 times. Magnesium sulfate was used to dehydrate the solution and to concentrate the organic layer. Subsequently a white solid was purified by column chromatography to give product. The solid was recrystallized in n-hexane. The yield of trinalbuphine trimesoyl ester was 9.1 g.

Example 22
Preparation of 1,3,5-cyclohexane triacid trinalbuphine ester 2 g of dinalbuphine hydrochloride and 10 ml of dichloromethane were added into a round flask. The flask was placed in an ice bath. After 5 minutes, then 1.76 ml of triethylamine and 5 ml of dichloromethane solution containing 0.46 g of 1,3,5 cyclohexane triacid chloride were added. Upon reaction for 30 minutes, the flask was moved from the ice bath to room temperature and stirring for another 30 minutes. The reaction was stopped in an ice bath for 5 minutes. Upon the formation of salt, the mixture was filtered, the filtrate was added with 20 ml of dichloromethane, followed by washing to 20 ml of saturated sodium chloride 3 times, and 20 ml of 5% citric acid twice. Magnesium sulfate was used to dehydrate the solution and to concentrate the organic layer. Subsequently a white solid was purified by column chromatography to give product. The molecular formula was determined to be $C_{72}H_{87}N_3O_{15}$, and the molecular weight determined to be 1234.49 for 3,3-dimethylglutaric dinalbuphine ester.

Example 23
Preparation of pyromellitoyl tetraNalbuphine ester 2 g of dinalbuphine hydrochloride and 10 ml of dichloromethane were added into a round flask. After 5 minutes, 1.76 ml of triethylamine and 5 ml of dichloromethane solution containing 0.42 g of pyromellitoyl chloride were added drop by drop. Upon reaction for 30 minutes, the flask was move from the ice bath to room temperature and continue the reaction for another 30 minutes.

The reaction was stopped in an ice bath for 5 minutes. Upon the formation of salt, the mixture was filtered, the filtrate was added to 20 ml of dichloromethane, followed by washing with 20 ml of saturated sodium chloride 3 times, and 20 ml of 5% citric acid twice. Magnesium sulfate was used to dehydrate the solution and to concentrate the organic layer. Subsequently a white solid was purified by column chromatography to give product. The molecular formula was determined to be $C_{94}H_{106}N_4O_{20}$, and the molecular weight determined to be 1611.88 for 3,3-pyromellitoyl tetranalbuphine ester.

Example 24
Preparation of injection solution 5 g of sebacoyl dinalbuphine ester was added to a 50 ml of sesame oil, subsequently 1.8 g of methyl paraben, 0.2 g of propyl paraben, 10 g of pluronic F68 were also added. The mixture was slightly shaking to form a saturated injection solution.

Example 25 to 36
Preparation of injection solutions 50 mg of sebacoyl dinalbuphine was added to a 2.8 ml of sesame oil, then appropriate excipients where listed in Table 4 was added subsequently. Procedures in example 24 were followed to prepare saturated injections.

TABLE 1

Adipoyl dinalbuphine ester

FAB MS($M^{+1}$) : 825 (Int, 29.92%),
$^1$H-NMR (DMSO)
 δ 6.80(d, 1H), 6.62(d, 1H), 4.8(s, 1H), 4.50(d, 1H),
  4.29(d, 1H), 4.0(broad, 1H), 3.0~1.0(broad),
$^{13}$C-NMR (DMSO)
 δ 171, 149, 132, 131, 130, 122, 118, 91, 69, 85, 61.9, 59.9,
  46, 42.9, 40.7, 40.3, 33.1, 32.8, 27.9, 26.5, 26.2, 23.7,
  22.9, 18.3
 IR– 3600–3100 cm$^{-1}$ broad band,
  3000–2800 cm$^{-1}$ C—H stretch, 1745 cm$^{-1}$ C-stretch.
  3600–3100 cm$^{-1}$ broad band,
  3000–2800 cm$^{-1}$ C—H stretch, 1745 cm$^{-1}$ C-stretch.
Suseroyl dinalbuphine ester MP: 104–105° C.
FAB MS($M^{+1}$) 853 (Int, 100%)
$^1$H-NMR (CDCl$_3$)
 δ 6.76(d, 1H), 6.62(d, 1H), 5.05(broad 1 H),
  4.64(d, 1H), 3.2–1.0(broad),
$^{13}$C-NMR (CDCl$_3$)
 δ 171.5(22), 148.4(3), 133.0(4), 131.3(12), 130.7(11),
  121.5(1), 118.7(2), 91.5(5), 70.0(14), 66.5(6),
  62.9(9), 60.5(17), 46.1(13), 43.6(16), 33.7, 33.6
  (23, 18), 32.0(15), 28.4(25), 26.7, 26.8(19, 21), 26.2
  (8), 24.6(24), 23.9(7), 23.3(10), 18.6(20)
 IR– 3700–3100 cm$^{-1}$ broad band '
  3000–2800 cm$^{-1}$ CH stretch ' 1760 cm$^{-1}$ C-stretch.
Sebacoyl dinalbuphine ester MP: 130–131° C.
FAB MS($M^{+1}$) 881 (Int 85%), TABLE 1-continued $^1$H-NMR(DMSO)
 δ 6.77(d, 1H), 6.60(d, 1H), 4.78(s, 1H), 4.49(d, 1H), 4.24
  (d, 1H), 4.0(m), 3,1~1.0 (broad band),
$^{13}$C-NMR (CDCl$_3$)
 δ 171.7(22), 148.5(3), 133.0(4), 131.1(12), 130.8(11),
  121.5(1), 118.8(2), 91.6(5), 70.0(14), 66.6(6), 62.9(9),
  60.6(17), 46,1(13), 43.7(16), 33.9(23), 33.6(18),
  32.0(15), 28.8, 28.9(25, 26), 26.9, 26.7(19, 21),
  26.2(8), 24.8(24), 23.9(7), 23.3(10), 18.7(20),
 IR– 3700~3100 cm$^{-1}$ (broad band)
  3000–2800 CH stretch, 1760 C-stretch.
Dodecauedioy dinalbuphine ester MP: 103–104° C.
FAB MS $M^{+1}$ = 909 (Int 100%),
$^1$H-NMR (DMSO)
 δ 6.76(d, 1H), 6.62(d, 1H), 4.63(s, 1H), 4.17, 3.7~
  1.0 (broad band),
$^{13}$C-NMR (CDCl$_3$),
 δ 171.7(22), 148.5(3), 133.0(4), 131.4(12), 130.7(11),
  121.5(1), 118.(2), 91.6(5), 70.0(14), 66.6(6), 63.0(9),
  60.6(17), 46.1(13), 43.7(16), 33.9(23), 33.6(18),
  32.0(15), 28.8, 28.9(25, 26), 26.9, 26.7(19, 21), 26.3(8),
  24.9(24), 24.0(7), 23.4(10), 18.7(20),
 IR– 3700–3100 cm$^{-1}$ (broad band),
  3000–2800 CH stretch, 1760 C-stretch.
Isophthaloyl dinalbuphine ester MP: 155~156° C.
FAB MS($M^{+1}$) 84.5 (Int 85%),
$^1$H-NMR (DMSO)
 δ 8.78(d, 1H), 8.46(d, 1H), 7.86(t, 1H), 7.01(d, 1H), 6.69
  (d, 1H), 4.81(s, 1H), 4.52(d, 1H), 4.43(d, 1H), 3.2–1.0
  (broad band),
$^{13}$C-NMR (DMSO)
 δ 162.9(22), 149.4(3), 135~129(23, 26, 4, 12, 11),
  122.2(1), 118.3(2), 91.7(5), 69.3(14),
 IR– 3700–3200 cm$^{-1}$ (broad band),
  3000~2750 C—H stretch, 1728 C-stretch.
Phthaloyl dinalbuphine ester MP: 137~138° C.
FAB MS($M^{+1}$) 845 (Int 31%),
$^1$H-NMR (CDCl$_3$)
 δ 8.3(s, 2H), 6.93(d, 1H), 6.71(d, 1H), 5,1(s), 4.68
  (d, 1H), 3.0~1.0(broad band),
$^{13}$C-NMR (CDCl$_3$)
 δ 163.3(22), 148.4(3), 133.3(4), 131.2(12), 130.4(11),
  121.5(1), 118.9(2), 91.8(5), 70.0(14), 66.5(6), 62.9(9),
  60.5(17), 46, 1(13), 43.7(16), 33.5(18), 32.0(15), 26.9,
  26.7(19, 21), 26.2(8), 23.9(7), 23.3(10), 18.6(20),
 IR– 3700~3200 cm$^{-1}$ (broad band),
  3000–2750 CH stretch, 1728 C-stretch.
1,3-cyclohexane diacid dinalbuphin ester FAB MS MH$^+$ = 850 (Int = 100%),
$^1$H-NMR (CDCl$_3$)
 δ 6.76(1H), 6.64(1H), 4.84(1H), 4.17(1H), 3.15~1.0(broad
  band)
$^{13}$C-NMR (CDCl$_3$)
 δ 171.6(22), 148.4(3), 133.1(4), 131.2(12), 131.0(11),
  121.4(1), 118.8(2), 91.7(5), 70.0(14), 66.5(6), 63.0(9),
  60.6(17), 46.1(13), 43.7(16), 41.7(23), 33.6(18), 32.0
  (15), 30.2(24), 26.9, 26.7, 26.3(19, 21, 25), 25.3(8)
  23.9, 23.4(7, 10), 18.7(20).
 IR– (KBr) 3700~3100 cm$^{-1}$ (broad band), 1750 C=O Stretch.
Docosanodic dinalbuphine ester FAB MS MH$^+$ = 1234 (Int = 30%)
FAB high resolution MS = $C_{64}H_{92}N_2O_{10}$
3,3-Dimethylglutaric diacid dinalbuphine ester FAB MS MH$^{+1}$ = 1234
$^1$H-NMR (CDCl$_3$)
 δ 6.79(d, 1H), 6.64(d, 1H), 4.64(d, 1H), 3,2–1.0 (broad band)
$^{13}$C-NMR (CDCl$_3$)

TABLE 1-continued

δ  171.6(22), 148.4(3), 133.1(4), 131.2(12), 131.0(11), 121.4(1), 118.8(2), 91.7(5), 70.0(14), 66.5(6), 63.0(9), 60.6(17), 46.1(13), 43.7(16), 41.7(23), 33.6(18), 32.0(15), 30.2(24), 26.9, 26.7, 26.3(19, 21, 25), 25.3(8), 23.9, 23.4 (7, 10), 18.7(20)

IR– (KBr) 3700~3100 cm$^{-1}$ (broad band), 3000~2800 C—H stretch, 1750 C=O stretch

Trimesoyl trinalbuphine ester

MP: 232–233° C.
FAB MS(M$^+$) 1228 (Int 50%),
$^1$H-NMR (CDCl$_3$)
  δ  9.24(s, 1H), 6.93(d, 1H), 6.71(d, 1H), 4.66(d, 1H), 3.2~1.0(broad band),
$^{13}$C-NMR (CDCl$_3$)
  δ  162.4(22), 148.3(3), 136.7~130.5(23, 24, 4, 11, 12), 121.4(1), 119.0(2), 91.9(5), 70.0(14), 66.6(6), 62.9(9), 60.5(17), 46.2(13), 43.7(16), 33.6(18), 32.1(15), 26.9, 26.7(19, 21), 26.3(8), 23.9(7), 23.4(10), 18.7(20),
IR– 3700~3200 cm$^{-1}$ (broad band, aromatic C—H sketch), 3000~2800 cm$^{-1}$, C—H stretch; 1740 cm$^{-1}$ C=O Stretch.

1,3,5,-Cyclohexane triacid trinalbuphine ester

FAB MS MH$^+$ = 1234,
$^1$H-NMR (CDCl$_3$)
  δ  6.79(d, 1H), 6.65(d, 1H), 4.65(d, 1H), 3,2~1.0(broad band)
IR– (KBr) 3700~3100 cm$^{-1}$ (broad band), 3000~2800 C—H stretch, 1750 C=O stretch.

Pyromellitoyl tetranalbuphine ester

FAB MS MH$^+$ = 1234 (Int = 48%),
$^1$H-NMR (CDCl$_3$)
δ 6.79(d, 1H), 6.65(d, 1H), 4.65(d, 1H), 3,2–1.0(broad band)
$^{13}$C-NMR (CDCl$_3$)
  δ  163.0(22), 148.5(3), 134.1(24), 133.2(4), 131.4(12), 131.0(11), 121.7(1), 118.8(2), 91.8(5), 70.0(14), 66.5(6), 64.4(23), 62.9(9), 60.6(17), 46.2(13), 43.6(16), 33.6(18), 32.2(15), 27.0, 26.8(19, 21), 25.3(8), 23.8, 23.5(7, 10), 18.7(20)
IR– (KBr) 3700~3100 cm$^{-1}$ (broad band), 3000~2800 C—H stretch, 1750 C=O stretch.

TABLE 2

| Samples of analysis | Elimination half-life (min) | Correlation coefficient of regression line |
|---|---|---|
| rat whole blood | 2.2 ± 0.5 | −0.98 ± 0.03 |
| rat plasma | 2.8 ± — | −0.994 ± — |
| rat red blood cell | 2.3 ± 0.6 | −0.95 ± 0.05 |
| rabbit whole blood | 14.9 ± 1.3 | −0.985 ± 0.003 |
| rabbit plasma | 6.98 ± 0.03 | −0.992 ± 0.002 |
| rabbit red blood cell | 26.2 ± 4.8 | −0.953 ± 0.03 | n = 3
Data = mean ± S.E.

TABLE 3

| Samples of analysis | Elimination half-life (min) | Correlation coefficient of regression line |
|---|---|---|
| dog whole blood | 30.5 ± 0.8 | −0.9943 ± 0.0008 |
| dog plasma | 27.8 ± 0.5 | −0.995 ± 0.003 |
| dog red blood cell | 33.4 ± 1.4 | −0.966 ± 0.007 |
| human whole blood | 8.8 ± 0.4 | −0.952 ± 0.003 |
| human plasma | 9.0 ± 0.4 | −0.93 ± 0.02 |
| human red blood cell | 7.7 ± 0.4 | −0.94 ± 0.03 | n = 3
Data = mean ± S.E.

TABLE 4

Batch Manufacturing Formula

| Quantity Example Unit/ Ingredients | Example | | | | | |
|---|---|---|---|---|---|---|
| batc | 24 | 25 | 26 | 27 | 28 | 29 |
| Sebacoyl Dinalbuphine Ester | 35 mg/ 0.7 g | 30 mg/ 3.0 g | 25 mg/ 2.5 g | 25 mg/ 2.5 g | 30 mg/ 3 g | 50 mg/ 5.0 g |
| Methyl paraben | | | | | | 1.8 mg/ 0.18 g |
| Propyl paraben | | | | | | 0.2 mg/ 0.02 g |
| Pluronic F68 | | | | | | |
| Pluronic HS15 | | | | | | |
| Span 85 | | | | | 0.2 mg/ 0.02 g | 0.2 mg/ 0.02 g | 0.2 mg/ 0.02 g |
| BHA | | | | | | |
| BHT | | | | | | |
| Cremophor EL | | | | | | |
| Sesame oil | 1 ml/ 20 ml | 1 ml/ 100 ml | 1 ml/ 100 ml | 1 ml/ 100 ml | 1 ml/ 100 ml | 1 ml/ 100 ml |
| Peanut oil | | | | | | |

※ Sebacoyl Dinalbuphine Ester lot No. A9611501

TABLE 5

Test Results of Sebacoyl Dinalbuphine ester oil Solution for I.M. injection

| | test Item | | Results | |
|---|---|---|---|---|
| Example | Appearance | Identification | Assay | Note |
| 24 | Pale yellow oily solution | pass | 99.5% | ⅔ vials with crystalline ppt |
| 25 | Pale yellow oily solution | pass | 105.2% | ⅔ vials with crystalline ppt |
| 26 | Pale yellow oily solution | pass | 97.0% 97.3% | |
| 27 | Pale yellow oily solution With white granulate ppt | pass | 101.2% 101.9% | 45° C. test with crystalline ppt |
| 28 | Pale yellow oily solution With crystalline ppt | pass | 103.0% 103.6% | 45° C., 1M, ½ vial crystalline ppt |
| 29 | Pale yellow oily solution | pass | 96.8% 95.7% | RT. 1M turbid solution |
| 30 | Pale yellow oily solution With crystalline ppt | pass | 107.0% 106.7% | |
| 31 | Pale yellow oily solution With crystalline ppt | pass | 102.2% | Temp ↑ crystalline ppt ↑ |
| 32 | Pale yellow oily solution | pass | 101.4% 101.3% | |
| 33 | Pale yellow oily solution | pass | 101.5% | |
| 34 | Pale yellow oily solution | pass | 106.1% | |
| 35 | Pale yellow oily solution | pass | 109.6% | SPAN 85 0.02% |

TABLE 6

| Parameters | Dog 1 | Dog 2 | Dog 3 | Dog 4 | Dog 5 | Mean | SD |
|---|---|---|---|---|---|---|---|
| A ($\mu$g/ml) | 20.9 | 14.1 | 9.5 | 14.1 | 16.5 | 15.0 | 4.2 |
| B ($\mu$g/ml) | 0.46 | 0.22 | 0.32 | 0.36 | 0.21 | 0.32 | 0.10 |
| $\alpha$ (1/h) | 8.54 | 6.85 | 23.02 | 4.76 | 6.74 | 9.98 | 7.41 |
| $\beta$ (1/h) | 0.063 | 0.023 | 0.024 | 0.022 | 0.019 | 0.030 | 0.019 |
| $k_o$ ($\mu$g/kg/h) | 129.9 | 149.9 | 199.1 | 249.5 | 174.9 | 180.6 | 46.4 |
| $t_{½,\alpha}$ (h) | 0.08 | 0.10 | 0.03 | 0.15 | 0.10 | 0.09 | 0.04 |
| $t_{½,\beta}$ (h) | 10.94 | 30.61 | 28.64 | 30.99 | 37.26 | 27.69 | 9.91 |
| Abs. time (h) | 164.5 | 95.6 | 49.3 | 58.0 | 95.6 | 92.6 | 45.4 |
| Vc (l/kg) | 13.88 | 10.21 | 14.95 | 10.65 | 24.50 | 14.84 | 5.77 |
| Vss (l/kg) | 360.9 | 450.1 | 428.1 | 303.6 | 1325 | 573.5 | 424 |
| k21 (1/h) | 0.25 | 0.13 | 0.78 | 0.14 | 0.10 | 0.28 | 0.29 |
| k10 (1/h) | 2.20 | 1.21 | 0.71 | 0.75 | 1.23 | 1.22 | 0.60 |
| k12 (1/h) | 6.16 | 5.53 | 21.55 | 3.89 | 5.43 | 8.51 | 7.34 |
| Cmax (ng/ml) | 59 | 112 | 197 | 255 | 123 | 149 | 77 |
| AUC (h·$\mu$g/ml) | 9.73 | 11.88 | 13.75 | 19.23 | 13.64 | 13.65 | 3.52 |
| F (%) | 87.9 | 59.0 | 40.4 | 59.6 | 68.8 | 63.1 | 17.3 |
| AUMC (h$^2$$\mu$g/ml) | 934.4 | 915.0 | 886.2 | 1217.4 | 1063.0 | 983.2 | 156.1 |
| MRT (h) | 84.3 | 78.8 | 61.1 | 62.7 | 79.1 | 73.2 | 10.6 |
| CLt (ml/h/kg) | 2.195 | 1.207 | 0.714 | 0.753 | 1.225 | 1.219 | 0.597 |

TABLE 7

| Parameters | Dog 2 | Dog 2 |
|---|---|---|
| Dose (mg/kg) | 24.3 | 81.0 |
| A ($\mu$g/ml) | 14.1 | 59.0 |
| B ($\mu$g/ml) | 0.22 | 0.51 |
| $\alpha$ (1/h) | 6.85 | 10.73 |
| $\beta$ (1/h) | 0.023 | 0.017 |
| $k_o$ ($\mu$g/kg/h) | 149.9 | 354.2 |
| $t_{½,\alpha}$ (h) | 0.10 | 0.07 |
| $t_{½,\beta}$ (h) | 30.6 | 41.9 |
| Abs. time (h) | 95.6 | 168.0 |
| Vc (l/kg) | 10.21 | 10.21 |
| Vss (l/kg) | 450.1 | 860.6 |
| k21 (1/h) | 0.13 | 0.11 |
| k10 (1/h) | 1.21 | 1.64 |
| k12 (1/h) | 5.53 | 8.99 |
| Cmax (ng/ml) | 1.12 | 204 |
| AUC (h·$\mu$g/ml) | 11.88 | 36.23 |
| AUC/D (h·kg/ml) | 0.478 | 0.488 |
| F (%) | 59.0 | 73.4 |
| AUMC (h$^2$ng/ml) | 915 | 5026 |
| MRT (h) | 78.8 | 127.2 |
| CLt (ml/h/kg) | 1.207 | 1.641 |

TABLE 8

| Example | starting material | product |
|---|---|---|
| 2 | pivaloyl chloride | Nalbuphine pivalate |
| 3 | benzoyl chloride | Nalbuphine benzoate |
| 4 | heptanoyl chloride | Nalbuphine enanthate |
| 5 | decanoyl chloride | Nalbuphine decanoate |
| 6 | behenic anhydride | Nalbuphine behenate |
| 7 | erucic anhydride | Nalbuphine erucicate |
| 8 | arachidic anhydride | Nalbuphine arachidate |
| 10 | suseroyl chloride | suseroyl dinalbuphine ester |
| 11 | sebacoyl chloride | sebacoyl dinalbuphin ester |

What we claim is:

1. A nalbuphine polyester derivative having a formula:

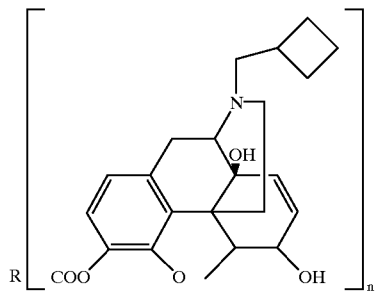

wherein n is an integer from 2 to 4, and
wherein R is a saturated or unsaturated aliphatic group.

2. The nalbuphine polyester derivative defined in claim 1, wherein said R group is an alkyl group having 1 to 40 carbon atoms.

3. The nalbuphine polyester derivative defined in claim 1 wherein R is selected form the group consisting of a branched-chain alkyl group, a straight-chained alkyl group substituted with a benzene ring, a branched-chain alkyl group substituted with a benzene ring, a benzenyl group substituted with a straight-chained aliphatic group, and a benzenyl group substituted with a branched-chain aliphatic group.

4. The nalbuphine polyester derivative defined in claim 2, wherein said alkyl group has 20 to 35 carbon atoms.

5. The nalbuphine polyester derivative defined in claim 4, wherein said alkyl group has 20 to 30 carbon atoms.

6. The nalbuphine polyester derivative defined in claim 1, wherein n is an integer of from 2 to 3.

7. An analgesic pharmaceutical composition comprising an effective amount of
the polyester derivative defined in claim 1, and a pharmaceutically acceptable carrier.

8. A method of treating an animal or human comprising administering to an animal or human in need thereof an effective amount of the derivative defined in claim 1.

9. The method defined in claim 8, wherein said derivative is administered buccally.

10. The method defined in claim 1,
wherein said derivative is administered sublingually.

11. The method defined in claim 1,
wherein said derivative is administered transdermally.

12. The method defined in claim 1,
wherein said derivative is administered intramuscularly.

13. The method defined in claim 1,
wherein said derivative is administered intravertebrately or by CFS.

14. A method for treating acute pain, chronic pain or addiction comprising
administering to an animal or human in need thereof an effective amount of the derivative defined in claim 1.

15. The analgesic pharmaceutical composition defined in claim 7
wherein said carrier is a 5% ethyl ester selected from the group consisting of peanut oil, soybean oil, and sesame oil.

16. The analgesic pharmaceutical composition defined in claim 7
wherein said carrier is a diluent or an oil.

17. The analgesic pharmaceutical composition defined in claim 7
wherein said carrier is suspended or dissolved in oil.

* * * * *

UNITED STATES PATENT AND TRADEMARK OFFICE
CERTIFICATE OF CORRECTION

PATENT NO. : 6,225,321 B1
DATED : May 1, 2001
INVENTOR(S) : Oliver Yoa-Pu Hu et al.

It is certified that error appears in the above-identified patent and that said Letters Patent is hereby corrected as shown below:

Title page,
Item [73], should read -- National Science Council, Taipei (TW) --.

Signed and Sealed this

Eighth Day of January, 2002

Attest:

JAMES E. ROGAN
Attesting Officer
Director of the United States Patent and Trademark Office